(12) United States Patent
Novikov et al.

(10) Patent No.: US 11,366,190 B2
(45) Date of Patent: Jun. 21, 2022

(54) SYSTEM, METHOD AND COMPUTER-ACCESSIBLE MEDIUM FOR CHARACTERIZING PROSTATE MICROSTRUCTURE USING WATER DIFFUSION AND NUCLEAR MAGNETIC RESONANCE RELAXATION

(71) Applicant: New York University, New York, NY (US)

(72) Inventors: Dmitry Novikov, New York, NY (US); Els Fieremans, New York, NY (US); Gregory Lemberskiy, Brooklyn, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 17/109,023

(22) Filed: Dec. 1, 2020

(65) Prior Publication Data
US 2021/0156944 A1 May 27, 2021

Related U.S. Application Data

(63) Continuation of application No. PCT/US2019/035211, filed on Jun. 3, 2018.
(Continued)

(51) Int. Cl.
*A61B 5/05* (2021.01)
*G01R 33/563* (2006.01)
(Continued)

(52) U.S. Cl.
CPC ........ *G01R 33/56341* (2013.01); *A61B 5/055* (2013.01); *A61B 5/4381* (2013.01);
(Continued)

(58) Field of Classification Search
CPC ....... A61B 5/055; A61B 5/4064; A61B 6/032; A61B 5/0042; A61B 2576/00
(Continued)

(56) References Cited

U.S. PATENT DOCUMENTS

| 2008/0108894 A1* | 5/2008 | Elgavish ............... G06T 19/00 600/420 |
| 2012/0095700 A1 | 4/2012 | Novikov et al. |

(Continued)

FOREIGN PATENT DOCUMENTS

| WO | 2006091983 | 8/2006 |
| WO | 2019063342 A1 | 4/2019 |

OTHER PUBLICATIONS

International Search Report for International Patent Application No. PCT/US2019/035211 dated Aug. 21, 2019.
(Continued)

*Primary Examiner* — Walter L Lindsay, Jr.
*Assistant Examiner* — Frederick Wenderoth
(74) *Attorney, Agent, or Firm* — Hunton Andrews Kurth LLP

(57) ABSTRACT

An exemplary system, method and computer-accessible medium for characterizing a microstructure of a prostate of a patient can be provided, which can include, for example, generating a magnetic resonance (MR) radiofrequency (RF) pulse(s) by varying (i) a diffusion time, (ii) a diffusion gradient direction, (iii) a diffusion gradient pulse width, or (iv) a diffusion gradient pulse shape, applying the MR RF pulse(s) to the prostate of the patient, receiving a resultant MR signal from the prostate of the patient that can be based on the MR RF pulse(s), determining information regarding a plurality of compartments for the prostate from the resultant MR signal by varying an echo time or a mixing time, and characterizing the microstructure for each of the com-
(Continued)

partments by applying a microstructural model(s) to each of the compartments.

23 Claims, 15 Drawing Sheets

Related U.S. Application Data

(60) Provisional application No. 62/679,237, filed on Jun. 1, 2018.

(51) Int. Cl.
*A61B 5/055* (2006.01)
*A61B 5/00* (2006.01)
*G01R 33/50* (2006.01)
*G01R 33/561* (2006.01)
*G01R 33/565* (2006.01)

(52) U.S. Cl.
CPC ......... *G01R 33/50* (2013.01); *G01R 33/5615* (2013.01); *G01R 33/56509* (2013.01)

(58) Field of Classification Search
USPC .......................................... 600/410; 324/309
See application file for complete search history.

(56) References Cited

U.S. PATENT DOCUMENTS

| | | | |
|---|---|---|---|
| 2012/0280686 A1* | 11/2012 | White | G01R 33/56341 324/309 |
| 2014/0167754 A1* | 6/2014 | Jerecic | G01R 33/56 324/309 |
| 2014/0218028 A1 | 8/2014 | Snyder et al. | |
| 2015/0055845 A1* | 2/2015 | Jensen | A61B 5/4088 382/131 |
| 2015/0228073 A1 | 8/2015 | Jensen et al. | |
| 2015/0279029 A1 | 10/2015 | Jensen et al. | |
| 2015/0309134 A1 | 10/2015 | Meakin et al. | |
| 2016/0343129 A1 | 11/2016 | Novikov et al. | |
| 2017/0089998 A1 | 3/2017 | Tran et al. | |
| 2017/0293008 A1* | 10/2017 | Qin | G01R 33/5607 |
| 2017/0340755 A1* | 11/2017 | Maiocchi | A61B 5/4325 |
| 2018/0055408 A1 | 3/2018 | Song et al. | |
| 2018/0335496 A1* | 11/2018 | Basser | G16H 10/40 |

OTHER PUBLICATIONS

International Written Opinion for International Patent Application No. PCT/US2019/035211 dated Aug. 21, 2019.
Supplementary European Search Report for European Patent Application No. EP 19812249 dated Feb. 7, 2022.

* cited by examiner

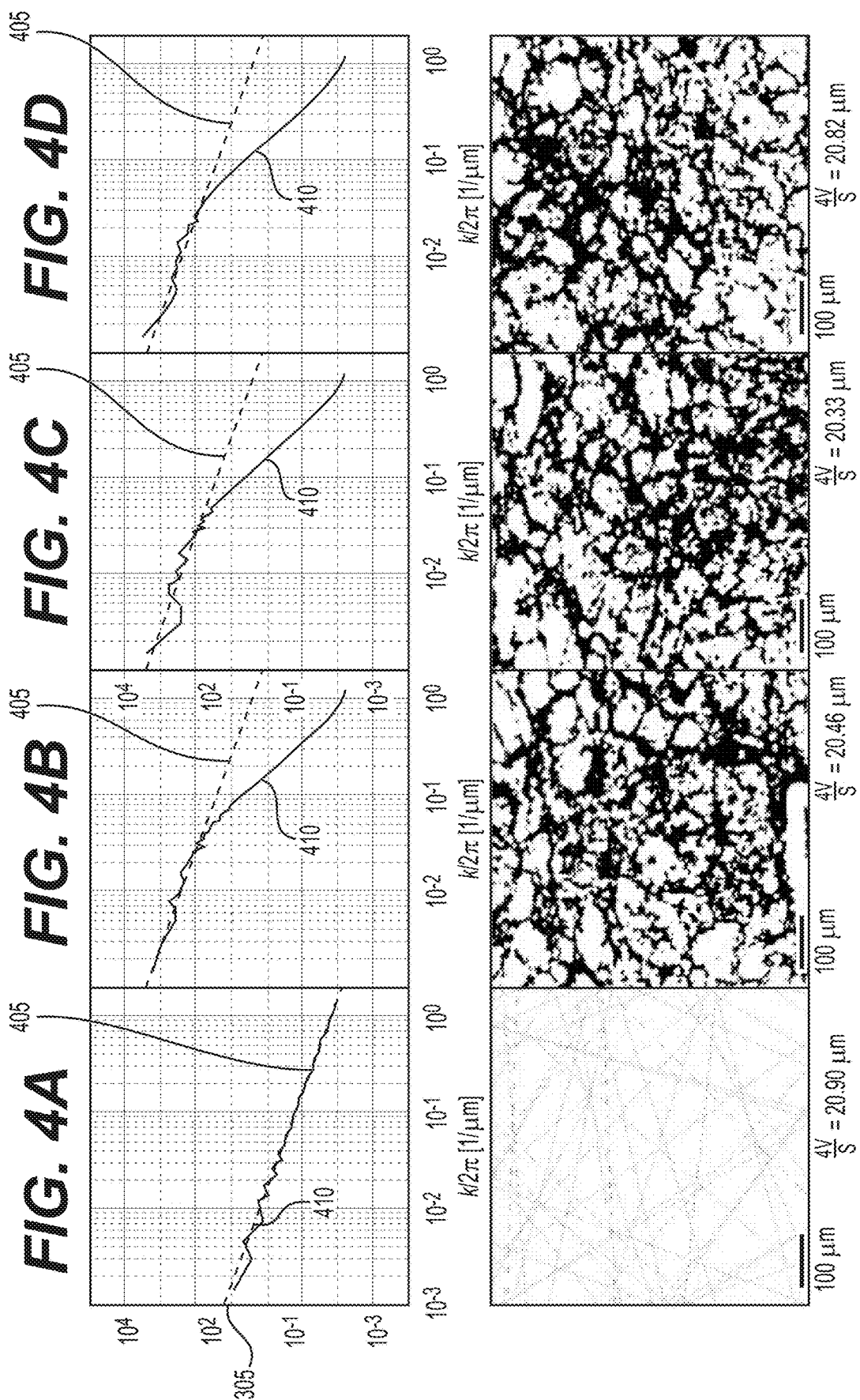

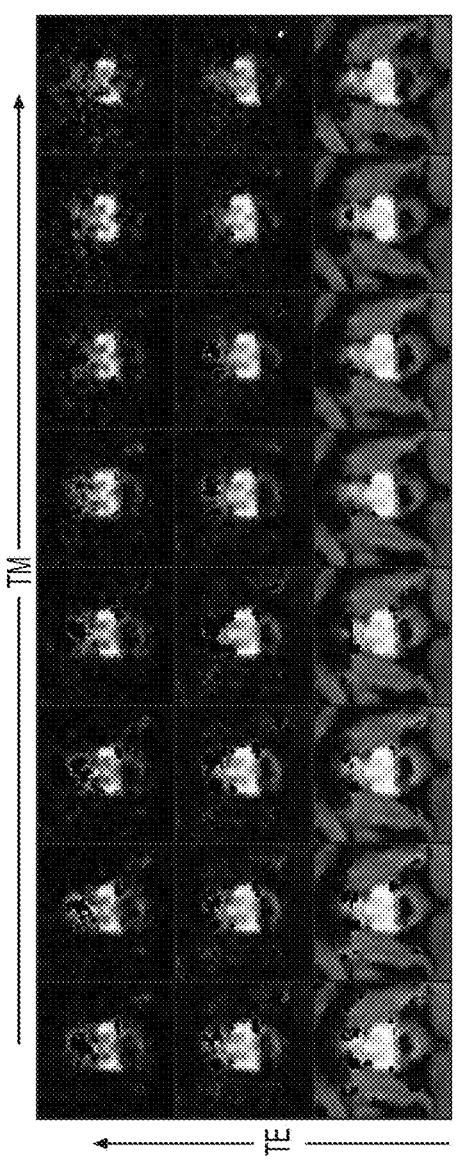
FIG. 5A
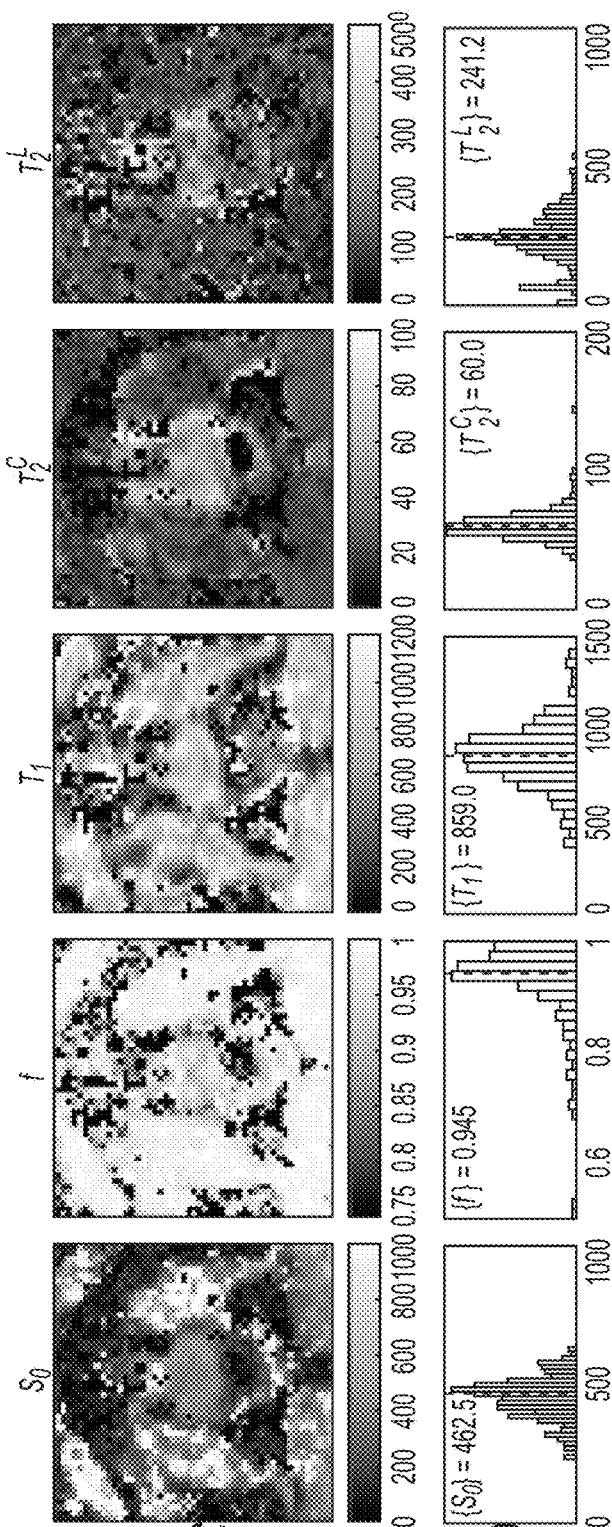
FIG. 5B
FIG. 5C
FIG. 5D

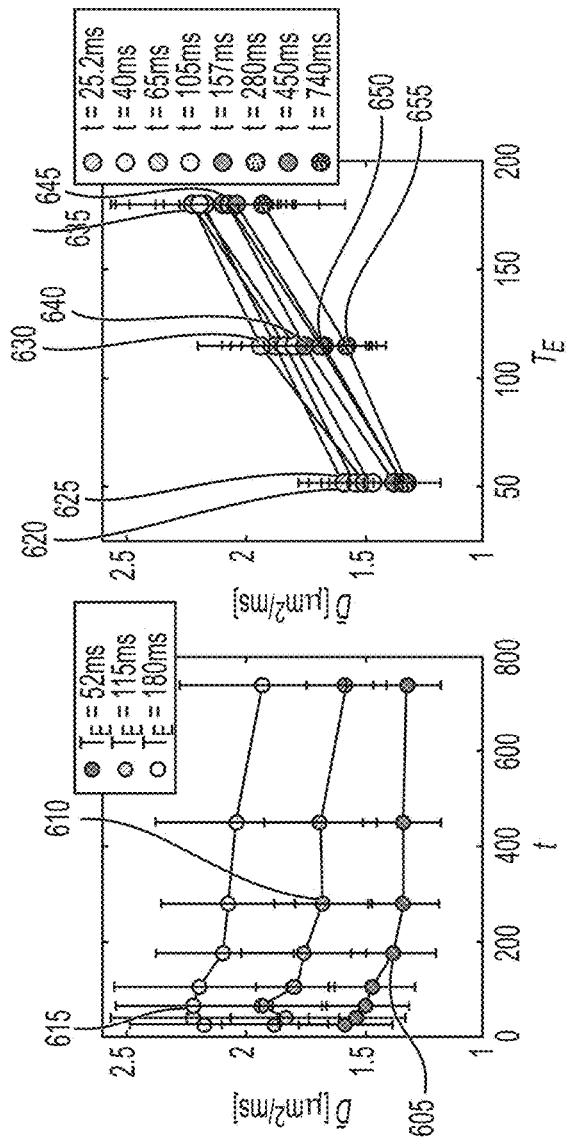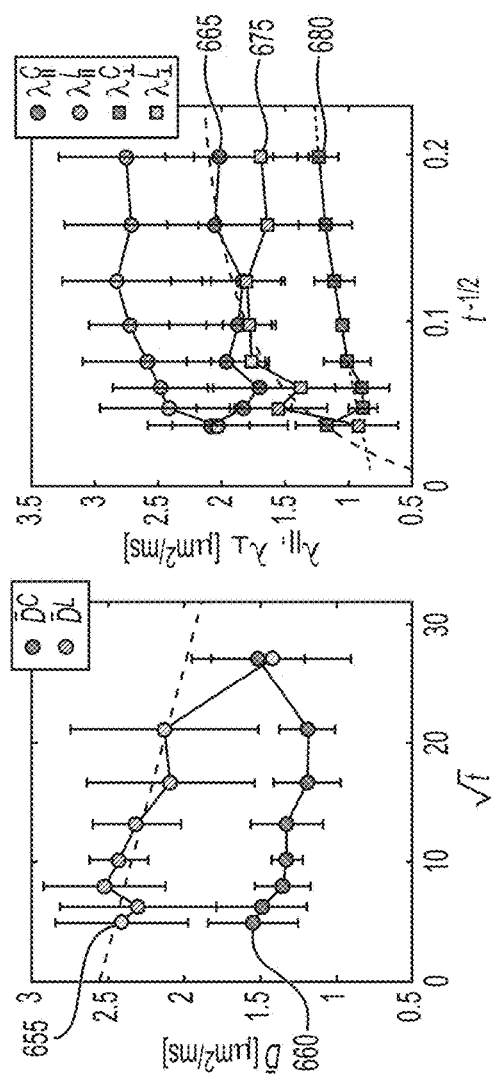

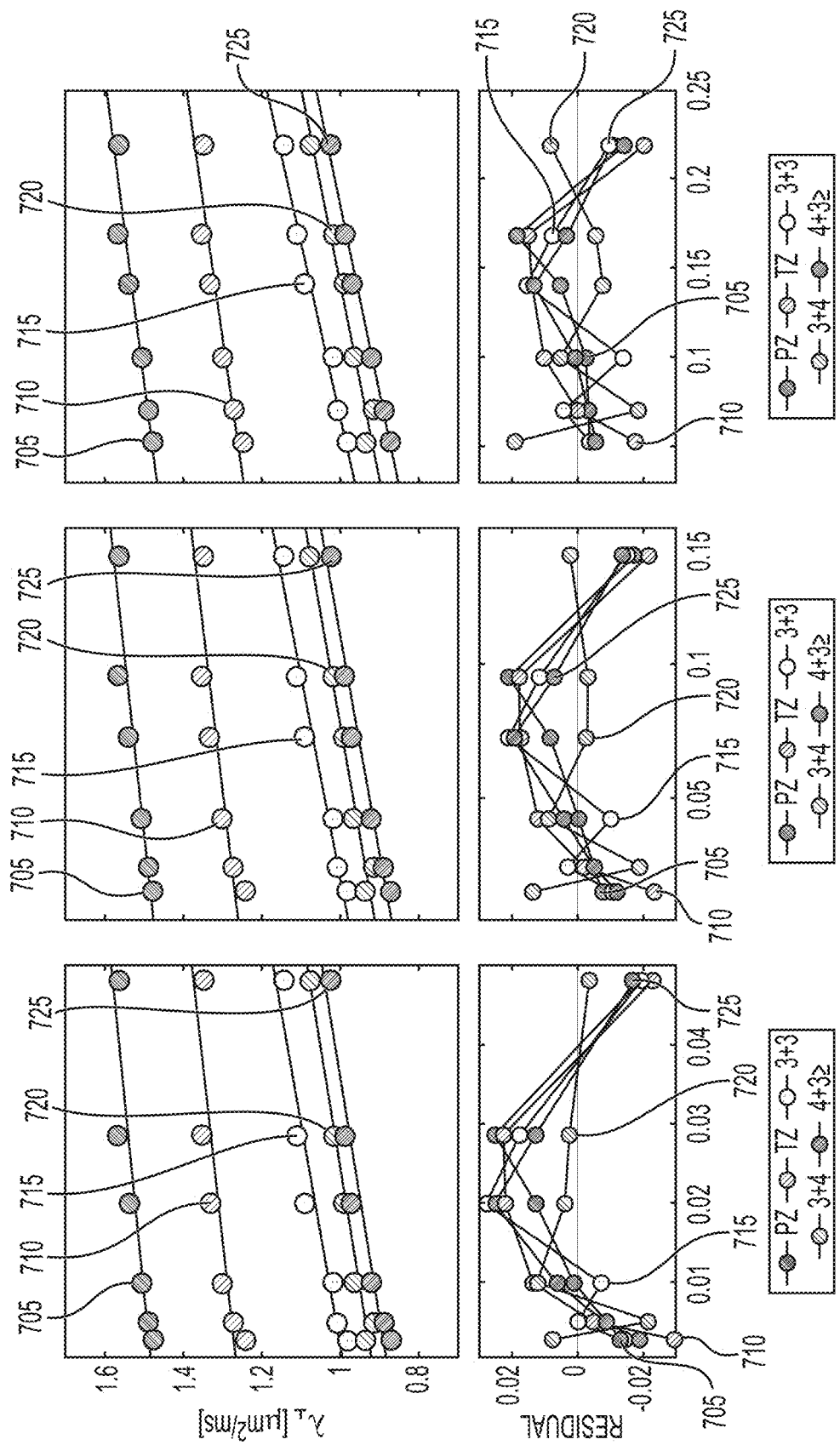

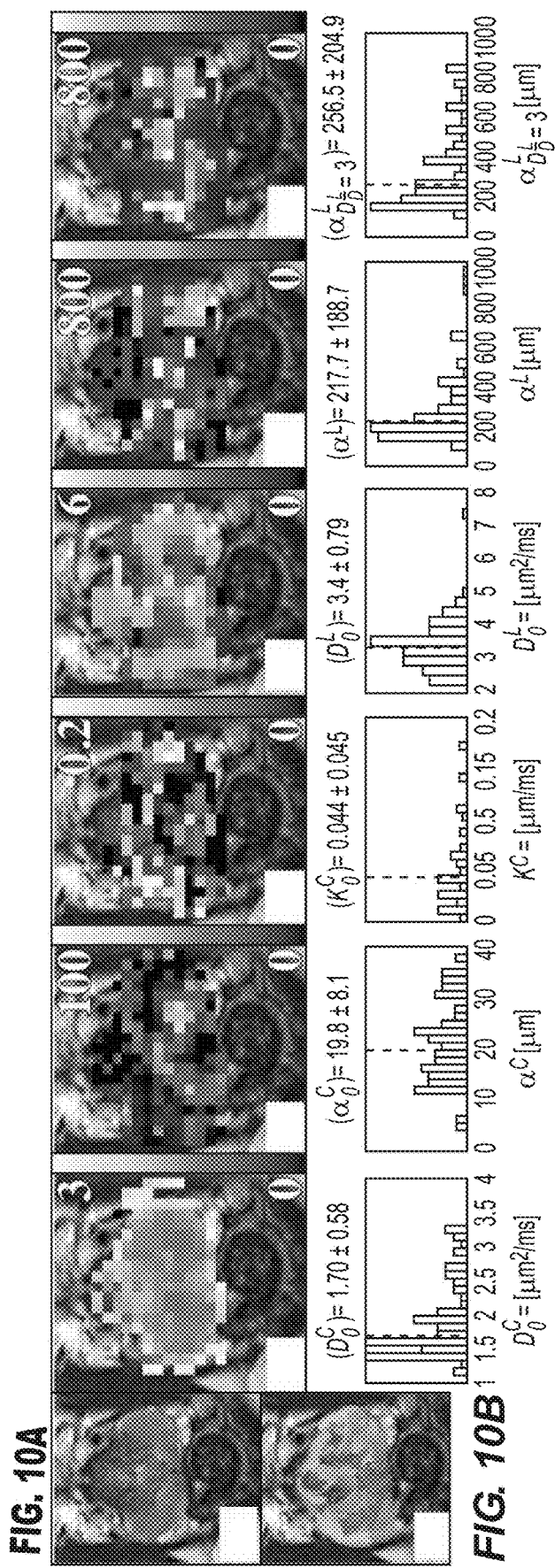

SYSTEM, METHOD AND COMPUTER-ACCESSIBLE MEDIUM FOR CHARACTERIZING PROSTATE MICROSTRUCTURE USING WATER DIFFUSION AND NUCLEAR MAGNETIC RESONANCE RELAXATION

CROSS-REFERENCE TO RELATED APPLICATION(S)

This application is a continuation of, relates to, and claims the benefit and priority from International Patent Application No. PCT/US2019/035211 filed on Jun. 3, 2019 that published as International Patent Publication No. WO 2019/232532 on Dec. 5, 2019, which claims the benefit and priority from U.S. Provisional Patent Application Ser. No. 62/679,237, filed on Jun. 1, 2018, the entire disclosures of which are incorporated herein by reference.

FIELD OF THE DISCLOSURE

The present disclosure relates generally to a prostate microstructure, and more specifically, to exemplary embodiments of an exemplary system, method and computer-accessible medium for characterization of prostate microstructure using water diffusion and nuclear magnetic resonance relaxation.

BACKGROUND INFORMATION

With the estimated 164,690 new prostate cancer ("PC") cases and 29,430 PC deaths in 2018 in the United States, (see, e.g., Reference 1), it is anticipated that approximately $13.5 billion will be spent this year for PC treatment. Despite its frequency (e.g., 1 man in 9 will be diagnosed with PC over lifetime), only 1 in 41 will die of PC. (See, e.g., Reference 1). Autopsy series have found that approximately ⅓ of men over age 50 have histologic evidence of PC, yet a large majority of these are clinically insignificant. (See, e.g., Reference 2). Over one million trans-rectal prostate biopsies are performed annually, even though the majority of them fail to detect PC. Thus, a non-invasive and more accurate diagnostic test is needed to identify clinically significant PC.

Radical prostatectomy ("RP") is a widely applied standard curative therapy for PC, but is currently regarded as over-treatment for many patients. It is estimated that 48 men must undergo RP to prevent 1 death over a 9-year period. (See, e.g., Reference 3). This data must be viewed in consideration of the negative impact of RP on quality-of-life: over 90% of RP patients reported sexual problems at the 3-year follow-up, over 50% had urinary problems. (See, e.g., Reference 4).

Distinguishing indolent and aggressive cancers would drastically reduce over-treatment by enabling appropriate selection of patients for radical therapy. Currently, the histological Gleason score ("GS") shows the greatest potential for this purpose. Despite the role of post-surgery-determined GS in predicting long-term outcome, there is no reliable way of identifying the GS pre-operatively, when treatment decisions are made. GS at biopsy is an unreliable predictor of GS at RP due to inaccurate sampling. In a study of 771 patients with low-grade PC on biopsy who underwent surgery, nearly half were upgraded to a higher GS after surgery. (See, e.g., Reference 5). Also, many men who select active surveillance based on biopsy GS harbor undetected high-grade PC. (See, e.g., Reference 6). The inability to confidently predict PC by biopsy is a primary cause for substantial over-treatment.

Magnetic resonance imaging ("MRI") represents the only widely utilized non-invasive imaging modality in clinical practice for localization of a tumor within the prostate. The prospect of quantitative MRI can be used to characterize tumor aggressiveness and reliably identify or exclude clinically significant cancer. Along with T2-weighted ("T2w") MRI, diffusion MRI ("dMRI") plays a role in prostate MRI interpretation (see, e.g., References 7-10), being designated by the American College of Radiology as clinical standard for guiding localization and risk assessment of focal peripheral zone ("PZ") lesions. (See e.g., Reference 11) dMRI facilitated the development of PI-RADSv2 (see, e.g., Reference 11), which is a standardized magnetic resonance ("MR") MR-based PC suspicion score system that combines dMRI, T2w, and dynamic contrast enhanced ("DCE") MRI to minimize mortality and overtreatment of PC by improving the confidence between benign and malignant PC. Nonetheless, systematic biopsy remains the standard of care in the United States, and while a lower PI-RADS score implies no need for targeted biopsy, a high PI-RADS score also warrants targeted biopsy of the lesion itself.

An MRI-derived analog of the GS is also currently lacking. While numerous studies of dMRI have identified an inverse correlation between the apparent diffusion coefficient ("ADC") and GS (see, e.g., References 12 and 13), it is insufficient to predict a grade in individual patients given substantial overlap between low-grade and high-grade tumors in past studies. In addition, while ADC appears to correlate with cellularity (see, e.g., References 14-16), GS is also influenced by a range of other factors including cell size, uniformity of cell size and shape, size of glandular spaces, extent of glandular differentiation, and the presence of intermixed histologic components such as benign stroma. (See, e.g., Reference 13).

ADC values have been shown to predict failure for patients on active surveillance, as well as biochemical recurrence following RP (see, e.g., References 17 and 18), which suggests that the ADC is more than just a reflection of the cellularity, and that dMRI has the potential to unlock specific biophysical tissue properties. Currently, the contrast of clinical ADC reflects an unknown mixture of such properties, which severely limits its diagnostic value. While dMRI is empirically sensitive, it is not specific towards microstructural tissue changes affecting GS. Achieving this long-desired specificity has served as an overarching inspiration (see, e.g., Reference 19) for microstructural mapping (see, e.g., References 20 and 21) with MRI.

Thus, it may be beneficial to provide an exemplary system, method and computer-accessible medium for characterization of prostate microstructure using water diffusion and nuclear magnetic resonance relaxation which can overcome at least some of the deficiencies described herein above.

SUMMARY OF EXEMPLARY EMBODIMENTS

An exemplary system, method and computer-accessible medium for characterizing a microstructure of a prostate of a patient can be provided, which can include, for example, generating at least one magnetic resonance (MR) radiofrequency (RF) pulse by varying at least one of (i) a diffusion time, (ii) a diffusion gradient strength, (iii) a diffusion gradient direction, (iv) a diffusion gradient pulse width, (v) a diffusion gradient pulse shape, (vi) an echo time, (vii) a mixing time, or (viii) a flip angle, applying the MR RF pulse(s) to the prostate of the patient, receiving a resultant MR signal from the prostate of the patient that can be based on the MR RF pulse(s), determining information regarding a plurality of compartments for the prostate from the resultant MR signal by varying an echo time or a mixing time, and characterizing the microstructure for each of the compartments by applying a microstructural model(s) to each of the compartments.

The contributions from different compartments can be determined by estimating relaxation parameters including, but not limited to a fraction f, relaxation times $T_1$ and $T_2$, for each compartment. The compartment weights (fractions) can be used to quantify diffusion tensor anisotropy and diffusion time dependence for each of the compartments from the overall diffusion measurement.

In some exemplary embodiments of the present disclosure, the diffusion tensor can be determined based on a diffusion weighting applied in a set of directions, for each of the compartments. The compartments can include (i) a glandular lumen compartment, (ii) a stroma compartment, (iii) an epithelium compartment, and (iv) a vascular compartment. The information regarding the compartments can be determined by estimating at least one of (i) a glandular lumen surface-to-volume ratio, (ii) a glandular lumen size, or (iii) a glandular lumen free diffusivity. The glandular lumen surface-to-volume ratio has a meaning of the surface area of glandular lumen walls divided by the glandular lumen volume.

The information regarding the compartments can be determined by estimating (i) a stromal surface-to-volume ratio, (ii) a stromal fiber diameter, (iii) a stromal membrane permeability, or (iv) a stromal intrinsic diffusivity. The information regarding the compartments can be determined by estimating (i) an epithelium cell size or (ii) an epithelium free diffusivity. The information regarding the compartments can be determined by estimating (i) the IntraVoxel Incoherent Motion pseudo-diffusion coefficient and a signal fraction.

In certain exemplary embodiments of the present disclosure, each of the compartments can include its own set of markers (biophysical parameters). The information regarding the compartments can be determined based on a compartment fraction of each of the compartments. A sum of the compartment fraction for each of the compartments can add up to 1. The information regarding the compartments can be determined based on a signal contribution of each of the compartments. A signal intensity of the compartments can be proportional to a proton density of the compartments. The signal intensity can be modified by varying a flip angle.

In some exemplary embodiments of the present disclosure, the microstructure model(s) can include a plurality of microstructure models, where each of the microstructure models can be associated with one of the compartments. The resultant MRI signal can be based on an estimated compartment weight for each of the compartments. Some of the parameters of the compartments can be determined based on intra-compartment diffusion non-Gaussianity. The parameters of the compartments can be determined based on a plurality of diffusion gradient waveforms.

Additionally, an exemplary system, method and computer-accessible medium for characterizing prostate tissue of a prostate of a patient, can include, for example generating a magnetic resonance (MR) radiofrequency (RF) and gradient pulse(s) by varying at least one of: an echo time, a diffusion wave vector and/or wave form; a diffusion time; and a stimulated echo mixing time, a flip angle, applying the MR RF and gradient pulse(s) to the prostate of the patient, receiving a resultant MR signal from the prostate of the patient that can be based on the MR RF pulse (s), characterizing the prostate tissue based on compartmental fractions f of the prostate, their respective T1 relaxation time, T2 relaxation time, and microstructural parameters of the prostate tissue compartments, by using the resultant MR signal.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 4A-FIG. 4D are exemplary graphs and corresponding histopathologies for the structural correlation of stroma according to an exemplary embodiment of the present disclosure;

FIG. 5A is an exemplary set of images of STEAM relaxometry for echo time and mixing time according to an exemplary embodiment of the present disclosure;

FIG. 5B is an exemplary graph fitting Eq. (2) below after averaging over a peripheral zone according to an exemplary embodiment of the present disclosure;

FIG. 5C is a set of exemplary parametric maps of five fitted parameters according to an exemplary embodiment of the present disclosure;

FIG. 5D is a set of exemplary histograms of a distribution of relaxation parameters according to an exemplary embodiment of the present disclosure;

FIG. 6A-FIG. 6D are exemplary graphs illustrating a separation of prostate tissue diffusivities from the overall diffusivity measured at different echo times $T_E$, to compartmental diffusion tensor eigenvalues, according to an exemplary embodiment of the present disclosure;

FIG. 7A-FIG. 7C are exemplary graphs illustrating model selection according to an exemplary embodiment of the present disclosure;

FIG. 10A-FIG. 10H are exemplary images, and corresponding graphs, of cellular and luminal parameters derived from D(t) according to an exemplary embodiment of the present disclosure.

Figures 1A, 1B:
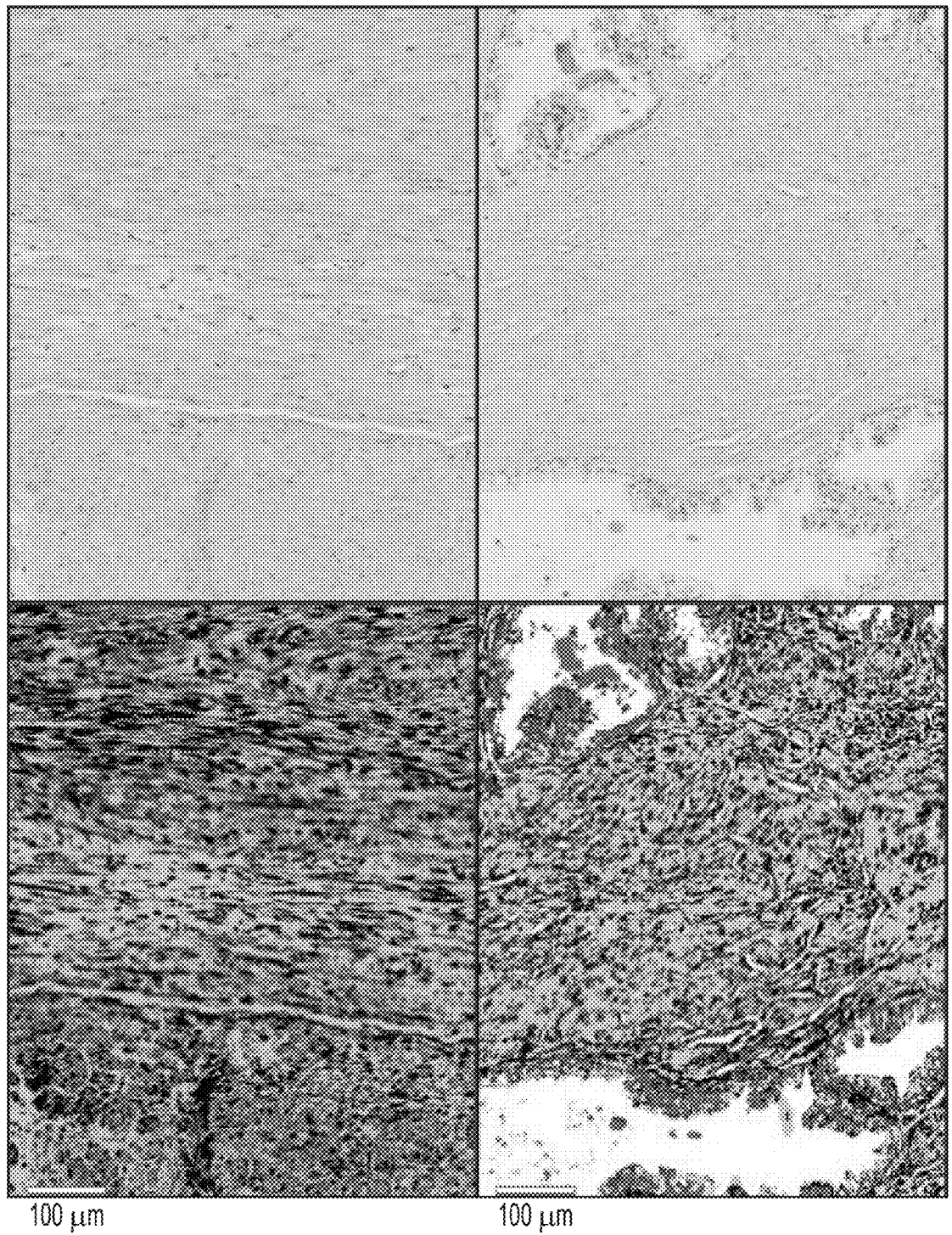
FIG. 1A and FIG. 1B are exemplary images of a prostate microstructure according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Recently, it was shown that the compartment fractions, rather than cellularity, can be GS determinants. (See, e.g., Reference 13). The exemplary system, method, and computer-accessible medium, according to an exemplary embodiment of the present disclosure, can be used to measure compartment-specific time-dependent diffusion tensors separately, together with the respective compartment fractions and their $T_2$ NMR relaxation times, by varying the echo time $T_E$, and diffusion time t, in addition to sampling the 3-dimensional dMRI $\vec{q}$-space. The compartmental $T_1$ relaxation time(s) can be obtained by varying the Stimulated Echo mixing time $T_M$. (See e.g., Reference 22). (See e.g., timing diagram shown in FIG. 3).

Figure 3:
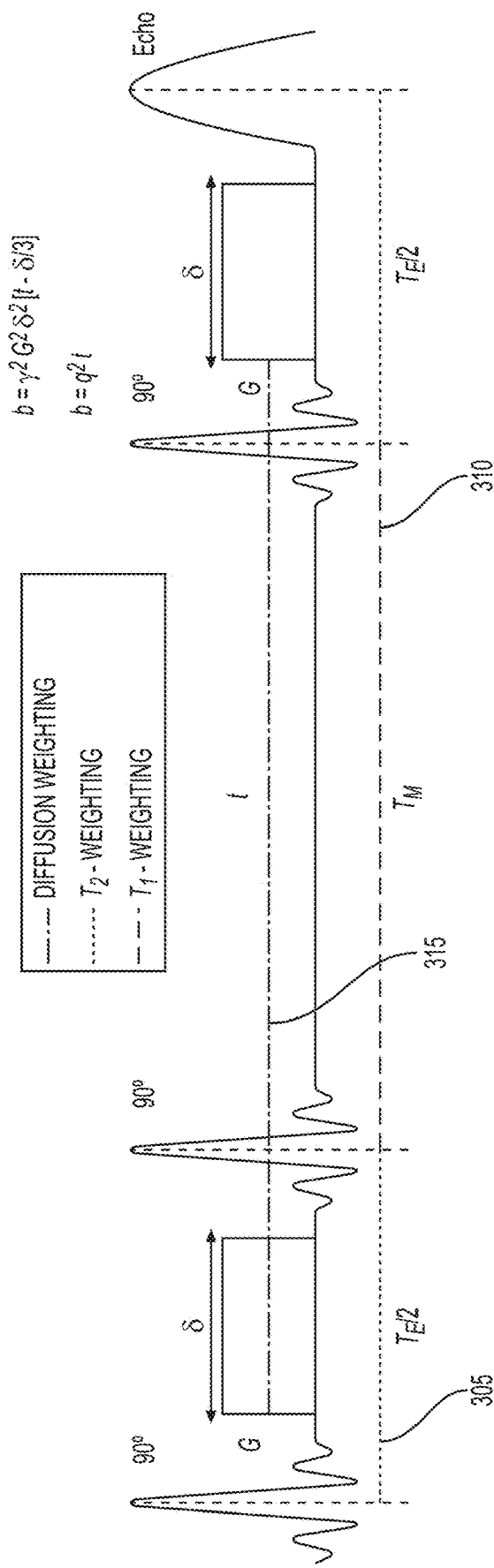
FIG. 3 is an exemplary timing diagram of an exemplary stimulated echo acquisition mode ("STEAM") according to an exemplary embodiment of the present disclosure.

FIG. 3 shows an exemplary timing diagram of an exemplary stimulated echo acquisition mode ("STEAM") according to an exemplary embodiment of the present disclosure, which illustrates the modification of parameters of NMR relaxometry, for example, T2 (e.g., line 305) and T1 (e.g., line 310) by varying the echo time, TE, and the mixing time, TM. Additionally, FIG. 3 illustrates the modification of parameters of diffusion weighting (e.g., line 315) by varying the applied gradient amplitude, G, the applied gradient duration, δ, and the spacing l between applied gradients. For example, the diffusion time t is approximately given by l; the accuracy is set by the value of δ. Further, the overall signal amplitude can be varied by varying the flip angle.

The tissue compartments can be, but not limited to, glandular lumen, stroma, epithelium, vascular (e.g., Intra-Voxel Incoherent Motion ("IVIM")), and others. Additionally, the exemplary system, method, and computer-accessible medium according to the present disclosure, can utilize diffusion time dependence of the compartment tensors to quantify tissue microstructure in each compartment. The role of the diffusion time t follows from the diffusion time dependence (see, e.g., Reference 23) of the overall diffusion tensor D(t) thus, 1. at least one compartmental diffusion tensor can depend on t (See e.g., graphs shown in FIG. 6A-FIG. 6D).
2. diffusion properties can vary across cancer grades (see e.g., graphs shown in FIG. 8A and FIG. 8B), where the lowest diffusivity can occur for high-grade tumors, and the fractional anisotropy can be highest for low-grade cancers. (See, e.g., Reference 23).
3. D(t) can illustrate best discrimination (see, e.g., Reference 23) between tumor grades at the shortest t, reaching an area under the curve ("AUC") for the receiver operating characteristic ("ROC") curve of 0.91.
4. t may not be fixed in a diffusion sequence, a source of variability between sites and vendors. (See, e.g., Reference 23). It can be beneficial to identify diagnostically optimal t and $T_E$ (e.g., to fix t).
5. time-dependence of diffusion tensors in each compartment can facilitate the quantification of the microstructure at a scale commensurate with the diffusion length $L(t)=\sqrt{6D(t)t}$. (See e.g., Reference 22).

FIG. 6A-FIG. 6D show exemplary graphs illustrating a separation of prostate tissue diffusivities according to an exemplary embodiment of the present disclosure. For example, the graph shown in FIG. 6A illustrates $T_E$=52 ms (line 605), $T_E$=115 ms (line 610), and $T_E$=180 ms (line 615). The graph provided in FIG. 6B illustrates t=25.2 ms (line 620), t=40 ms (line 625), t=65 ms (line 630), t=105 ms (line 635), t=175 ms (line 640), t=280 ms (line 645), t=450 ms (line 650), and t=740 ms (line 655). The graph shown in FIG. 6C illustrates $\overline{D}_C$ (line 655) and $\overline{D}_L$ (line 660). The graph shown in FIG. 6D illustrates $\lambda_\|^C$ (line 665), $\lambda_\|^L$ (line 670), $\lambda_\perp^C$ (line 675), and $\lambda_\perp^C$ (line 680).

FIG. 7A-FIG. 7C show exemplary graphs illustrating model selection according to an exemplary embodiment of the present disclosure. For example, the graphs shown in FIG. 7A-FIG. 7C illustrate PZ (line 705), TZ (line 710), 3+3 (line 715), 3+4 (line 720), and 4+3≥(line 725).

Figures 8A, 8B:
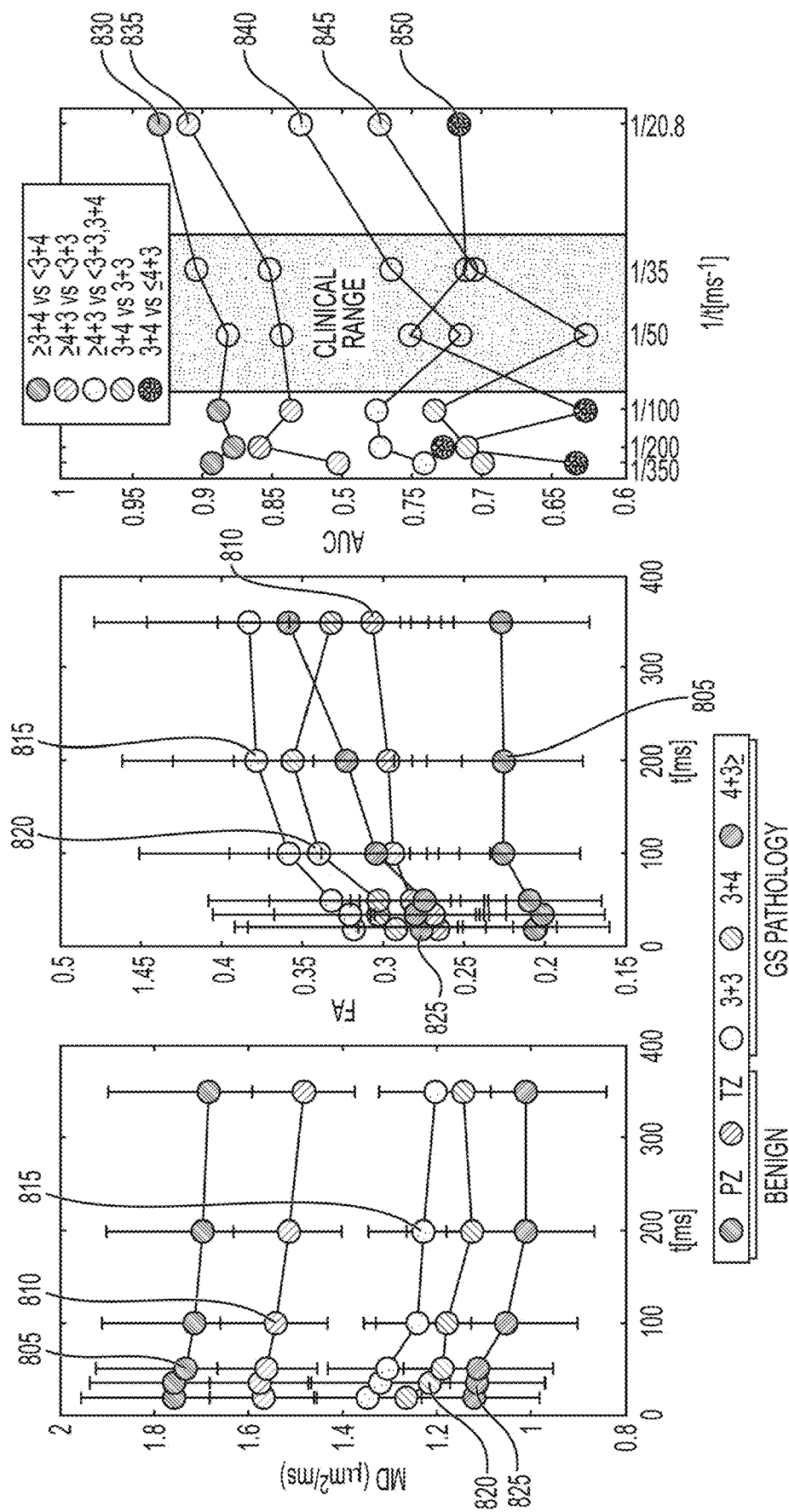
FIG. 8A is a set of exemplary graphs illustrating a diffusion time dependence of diffusion tensor imaging according to an exemplary embodiment of the present disclosure.
FIG. 8B is an exemplary graph illustrating areas under the receiver operating characteristic curve for discriminating between GS's increase according to an exemplary embodiment of the present disclosure.
Figures 9A, 9B, 9C, 9D, 9E, 9F, 9G, 9H, 9I:
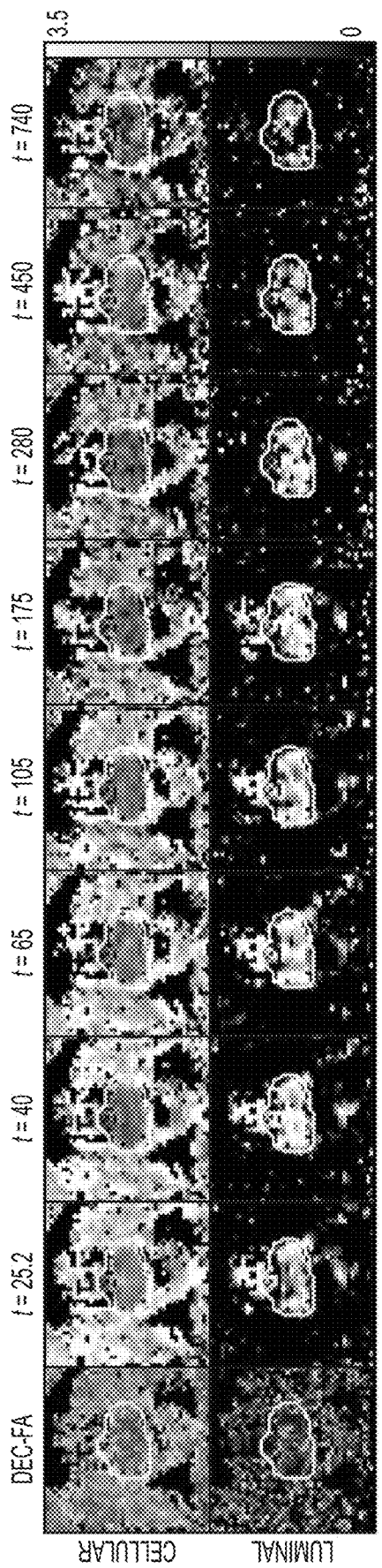
FIG. 9A-FIG. 9I are exemplary images and corresponding maps of compartment parameters derived from a diffusion tensor according to an exemplary embodiment of the present disclosure.

FIG. 8A shows a set of exemplary graphs illustrating diffusion time dependence of diffusion tensor imaging ("DTI") for fixed $T_E$=40.4 ms, in benign and pathological prostates (e.g., 38 total subjects) according to an exemplary embodiment of the present disclosure. For example, the graphs shown in FIG. 8A illustrate timing for PZ (line 805), transition zone ("TZ") (line 810), 3+3 (line 815), 3+4 (line 820), and 4+3 (line 825). FIG. 8B shows an exemplary graph illustrating areas under the ROC curve for discriminating between GS's increase for shorter t, reaching AUC=0.93 for diagnosing clinically significant tumors, at t=20.8 ms according to an exemplary embodiment of the present disclosure. For example, the graph shown in FIG. 8B illustrates GS≥3+4 vs. GS<3+4 (line 830), GS≥4+3 vs. 3+3 (line 835), GS≥4+3 vs. 3+3, 3+4 (line 840), 3+4 vs. 3+3 (line 845), and 3+4 vs. ≥4+3 (line 850).

Figure 2:
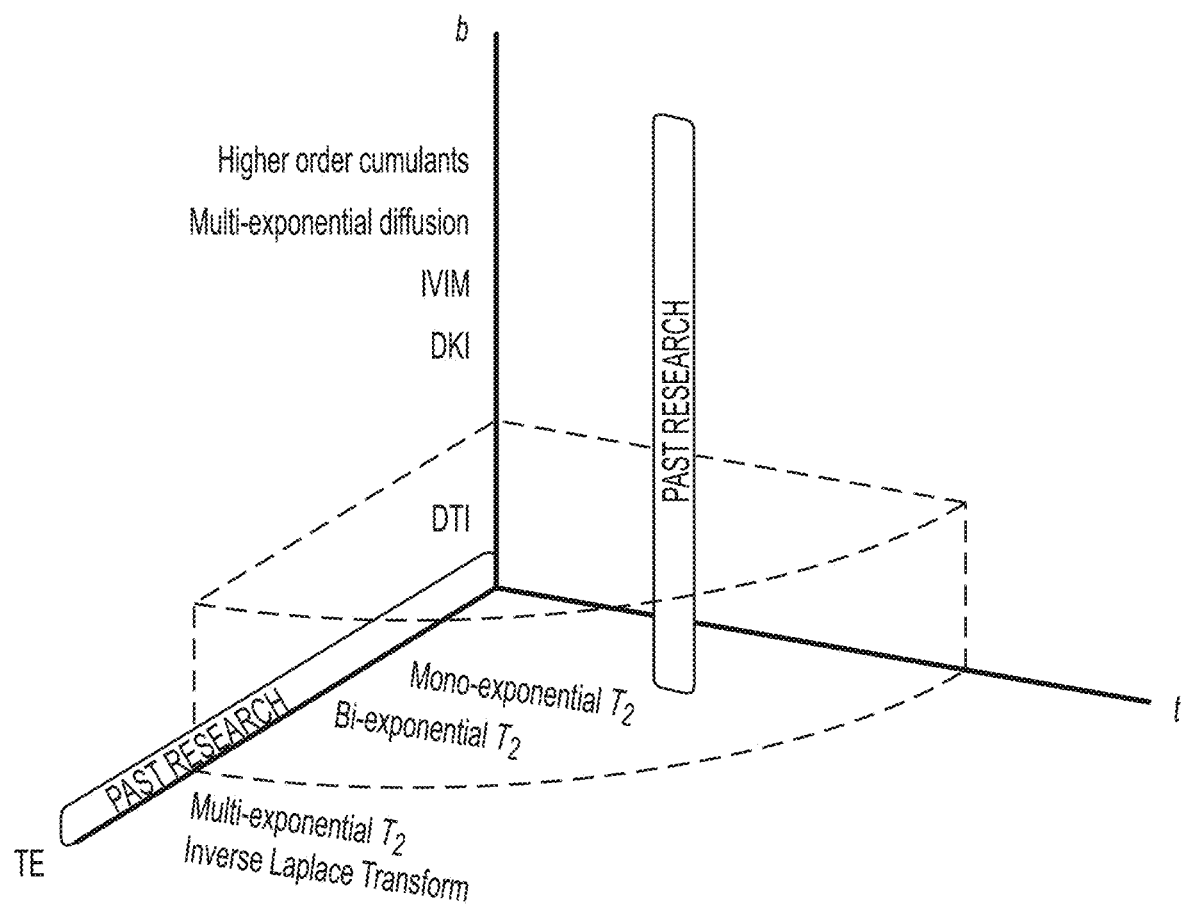
FIG. 2 is an exemplary graph of a parameter space of a multi-dimensional MRI according to an exemplary embodiment of the present disclosure.

FIG. 2 shows an exemplary graph of a parameter space of a multi-dimensional MRI according to an exemplary embodiment of the present disclosure. Various exemplary modeling approaches can be compared to determine the "correct" model using fit quality, which can include (i) mono-exponential (see, e.g., References 24 and 25), (ii) bi-exponential (see, e.g., References 26 and 27), (iii) empirical fourth-order cumulant (e.g., kurtosis). (See, e.g., Reference 28). However, various other suitable mono-exponential representations of diffusion (e.g., at fixed t) can fit clinical data reasonably well.

The luminal compartment can have a small volume fraction in the average MRI voxel (e.g., <10%) (see, e.g., Reference 34), yet due to its much longer $T_2$, it can contribute to the overall signal, as discussed below. Additionally, the distinct geometry (see, e.g., References 35 and 36) of the prostate tissue compartments can give rise to distinct (e.g., generally, time-dependent) diffusion tensors in the cellular (e.g., stromal, epithelial), in the vascular, and in the luminal compartments, respectively. The glandular lumen fraction can be about 3-10% and cellular (e.g., stroma, epithelium) can be the remaining amount. The vascular fraction can be practically negligible; in some exemplary embodiments it can be estimated, depending on the quality of the data.

Multidimensional MRI with Realistic Non-Gaussian Tissue Compartments

The following exemplary diffusion-relaxation model can be introduced in the multi-dimensional parameter space: diffusion vector $\vec{q}$, diffusion time t, echo time $T_E$, and, if using Stimulated Echo diffusion sequence, also the mixing time $T_M$, with the signal as a sum of (e.g., generally non-Gaussian) contributions with distinct relaxation times:

$$S(\vec{q}, t, T_M, T_E) = S_0 \cdot \sum_{f_n} e^{-\frac{T_g}{T_1^n} - \frac{T_M}{T_2^n} - bD^{(n)}(t) + O(b^2)}, \quad (1)$$

$$bD^{(n)} \equiv \sum_{ij} q_i q_j t \cdot D_{ij}^n(t), \text{ and}$$

$$\sum_n f_n = 1.$$

There can be a more general expression of the b-tensor in Eq. (1) based on the gradient wave form, for example, $b_{ij}=\int q_i(t)q_j(t)dt$.

The signal contributions of the sub-voxel tissue compartments can be separated, such as but not limited to the stromal, epithelium, luminal, and IVIM compartments, where each compartment can have an associated volume fraction, $f_n$, that can add up to 1. The overall signal intensity $S_0$ can be proportional to the proton density. Additionally, $S_0$ can be further modified by varying the flip angle. The compartments' fractions f, NMR relaxation times $T_1$ and $T_2$, can be estimated; also, the diffusion tensors can be estimated as a function of diffusion time. The tissue microstructure in each compartment can be separately quantified, based on particular compartment-specific microstructural models.

The exemplary system, method, and computer-accessible medium, according to an exemplary embodiment of the present disclosure, can also be used for other organs and/or tissues, where the joint NMR relaxation and diffusion measurements can be used to disentangle between compartment contributions, even in the case when at least one of them can be characterized by non-Gaussian (e.g., time-dependent) diffusion.

Separating Between Tissue Compartments

The exemplary model, provided in Eq. (1), can be used to, for example, estimate tissue compartment parameters from the multi-dimensional MRI data. However, such estimation (e.g., "fitting") can be unstable. To resolve this, multi-dimensional MRI data, and careful fit initialization, can be used based on the estimated compartment weights.

The exemplary realistic model can include notable diffusion time-dependence of diffusion tensors in each compartment. (See, e.g., Reference 23). The time-dependence can introduce non-Gaussian diffusion in each tissue compartment. (See, e.g., Reference 37). This can create a preference to resolve the intra-compartment diffusion non-Gaussianity, which has so far been ignored in previous approaches, and can lead to biased parameter estimation and interpretation. Accounting for the time-dependent diffusion in each compartment can facilitate the exemplary system, method and computer-accessible medium to be qualitatively distinct from previous empirical approaches that consider only Gaussian compartments (see, e.g., Reference 38), fix some of their parameters (see, e.g., References 38-41), and/or attribute non-Gaussianity solely to a fully restricted compartment. (See, e.g., References 39-41).

It can be beneficial to remain at low b (e.g., to operate within the diffusion tensor imaging, or DTI, regime), which can facilitate avoiding modeling the higher-order terms $O(b^2)$ in each exponential in Eq. (1), thereby, reducing the model complexity and achieving precise and unbiased results, and which can also make acquisition less demanding. Thus, the compartment diffusion tensors $D_{ij}^{(n)}(t)$ can be estimated, where $bD^{(n)} \equiv \sum_{ij} q_i q_j D_{ij}^{(n)}(t) \cdot t$ can be the diffusion weighting in direction $\vec{q}$ for each compartment. Time-dependence of diffusion tensors $D_{ij}^{(n)}(t)$ in the exemplary system, method and computer-accessible medium can be examined by varying the diffusion time (e.g., via the mixing time $T_M$ of the stimulated echo sequence, or by varying the time between diffusion gradients in a pulse-gradient spin-echo diffusion sequence).

Furthermore, it can be beneficial to utilize general diffusion gradient waveforms q(t), where the direction and magnitude of the diffusion gradient can vary in the full three-dimensional space for an added robustness in encoding the diffusion signals from each compartment, for separating their contributions, and for adding independent measurements for more robust parameter estimation of compartmental microstructural models.

Exemplary Estimation of Compartment Fractions, Relaxation Times and Diffusion Tensors As an example, two major prostate tissue compartments can be considered, such that the signal can be decomposed into cellular=(stroma+epithelium) and luminal compartments. Thus, the sum in Eq. (1) can be over 2 compartments, n=C and L. The generalizations for more than 2 compartments (as described above) can be evident.

Figure 1C:
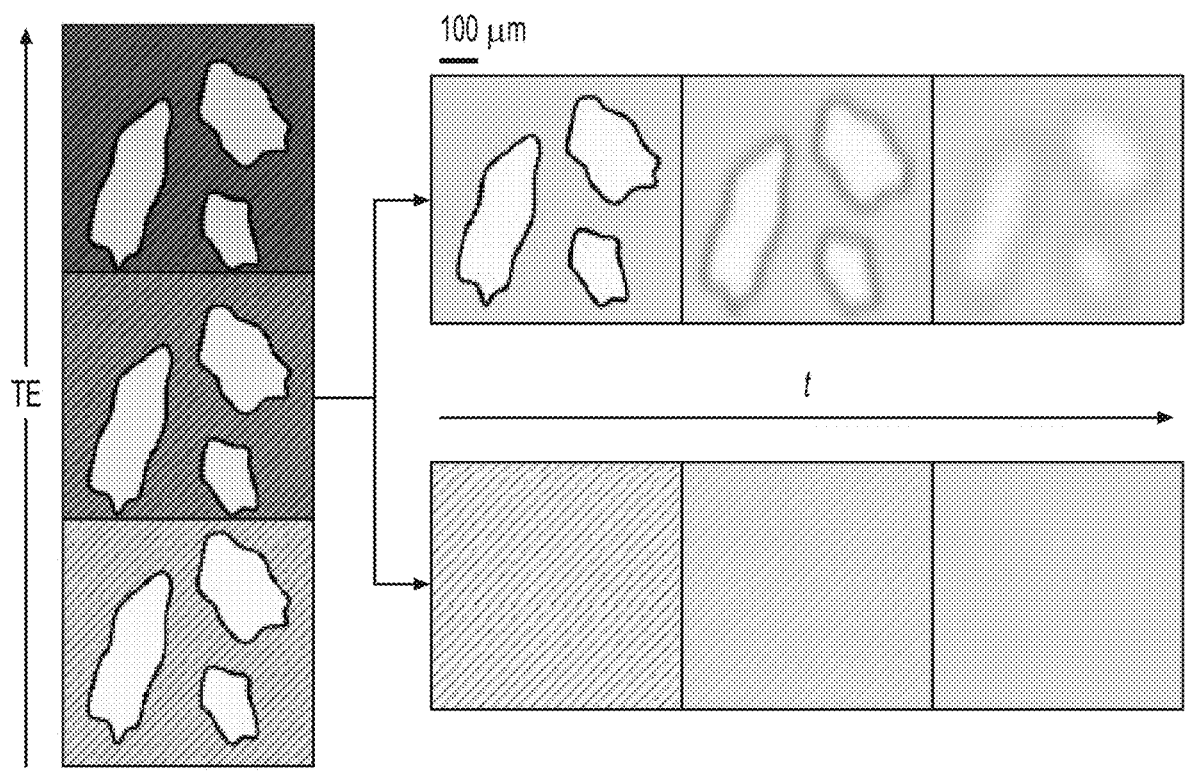
FIG. 1C is an exemplary diagram of a prostate microstructure according to an exemplary embodiment of the present disclosure.

Due to the difference in $1/T_2^{(n)}$ relaxation rates, the cellular compartment can lose its signal much faster than the luminal compartment with increasing echo time $T_E$, thereby creating a large dynamic range that can facilitate the separation of tissue compartments and their diffusion properties, as shown in the images of FIG. 1A-FIG. 1C. Performing diffusion measurements at different echo time $T_E$ can by itself become more informative and sensitive to the GS, which can be used to train an exemplary machine learning classifier based on at least one of echo time $T_E$, diffusion time, diffusion wave vector or wave form, and mixing time. The b-value can be kept low, to stay in the diffusion tensor regime (e.g., effectively factoring out the q-dependence of the signal), and to vary the diffusion time, and/or the mixing time $T_M$ of the stimulated echo sequence. This can also facilitate determining of the $T_1$ component, which has been shown to be a valuable biomarker for detecting post-biopsy hemorrhage (see, e.g., Reference 42) and to examine diffusion tensors such as, but not limited to, the cellular and luminal compartments ($D_{ij}^C(t)$ and $D_{ij}^L(t)$) separately.

It can be assumed that there can be the same $T_1$ for both compartments. If a constant repetition time ($T_R$) can be maintained, and perfect π/2 RF pulses can be assumed, the signal evolution for a stimulated echo ("STEAM") acquisition, without diffusion weighting can be written as, for example:

$$S|_{b=0}(T_M, T_E) = S_0 e^{-T_M/T_1} \left( \underbrace{f e^{-T_E/T_2^C}}_{C} + \underbrace{(1-f) e^{-T_E/T_2^L}}_{L} \right), \quad (2)$$

The weighted linear least squares (see, e.g., Reference 43) can be used to estimate the parameters ($S_0$, f, $T_2^C$, $T_2^L$, $T_1$) from the un-weighted $S|_{b=0}$ values measured for the range of $T_M$ and $T_E$, by fitting of Eq. (2) to the data.

The relative compartment weights for each $T_M$ and $T_E$ can be determined (e.g., with C and L from Eq. (2)), as for example:

$$W^C \equiv W(T_E) = \frac{C(T_E)}{C(T_R) + L(T_R)}, \quad W^L = 1 - W. \quad (3)$$

Expanding Eq. (1) up to O(b), the weights in Eq. (3) can relate the overall diffusion coefficient in a given direction where, for example:

$$D(t, T_E) = W^C(T_E) \cdot D^C(t) + W^L(T_E) \cdot D^L(t) \quad (4)$$

to the directional diffusion coefficients in each compartment. For a number N of distinct $T_E$ measurements, Eq. (4) reads, for example, as follows:

$$\begin{bmatrix} D(t, T_{E_1}) \\ D(t, T_{E_2}) \\ \vdots \\ D(t, T_{E_N}) \end{bmatrix} = W \begin{pmatrix} D^C(t) \\ D^L(t) \end{pmatrix}, \quad (5)$$

$$W = \begin{bmatrix} W^C(T_{E_1}) & W^L(T_{E_1}) \\ W^C(T_{E_2}) & W^L(T_{E_2}) \\ \vdots & \vdots \\ W^C(T_{E_N}) & W^L(T_{E_N}) \end{bmatrix}.$$

Using the fact that the weights can depend on $T_E$ but not on t, while the compartment diffusivities (e.g., in any given diffusion direction) can depend on t but not on $T_E$, $D^C(t)$ and $D^L(t)$ (e.g., in any given direction) can be determined separately for each t using, for example, matrix pseudo-inversion $W^{-1}$, as $$\begin{pmatrix} D^C(t) \\ D^L(t) \end{pmatrix} = W^{-1} \begin{bmatrix} D(t, T_{E_1}) \\ D(t, T_{E_2}) \\ \vdots \\ D(t, T_{E_N}) \end{bmatrix}. \quad (6)$$

FIG. 1A and FIG. 1B show exemplary images of prostate microstructure and FIG. 1C shows an exemplary diagram of prostate microstructure, according to an exemplary embodiment of the present disclosure. In the exemplary case, the number of different $T_E$ measurements was N=3. The results are shown in FIG. 5D. From the directional compartment diffusivities, the tensors $D_{ij}^C(t)$ and $D_{ij}^L(t)$ can be reconstructed. (See e.g., Reference 44). This exemplary parameter estimation procedure can be generalized to be used on more than 2 compartments. Other suitable procedures (such as, but not limited to, creating a library of signal combinations, according to, for example, Eq. (2), and performing a library search; such search can be either exhaustive, or via interpolating such library via a suitable nonlinear function, such as, but not limited to, a neural network) can also be used to estimate the compartment parameters.

Exemplary Compartment Tensor Eigenvalues and Fiber Tracking

Each set of compartment directional diffusivities can be processed using a suitable DTI procedure (see, e.g., Reference 45) with various weights. (See, e.g., Reference 43). To generate the diffusion tensors, the associated eigenvectors ($V_1$, $V_2$, $V_3$) eigenvalues ($\lambda_1$, $\lambda_2$, $\lambda_3$) and fractional anisotropy ("FA"), over each t can be used. Eigenvalues for each t can be averaged to produce mean diffusivity, $\overline{D}(t)$. (See, e.g., FIG. 9B-FIG. 9I).

FA(t) can increase with t. (See, e.g., References 23 and 46). The anisotropy of the diffusion tensor can become more apparent at longer diffusion times, driven by the fact that the differences between the physics of diffusion in different directions can become more apparent with coarse-graining tissue properties over larger distances.

Orientation in each eigenvector can be independent of t, as it can be produced by the same underlying tissue anisotropy. Given this orientation redundancy, an averaged orientation can be derived from the mean dyadic tensor computed across different values of diffusion time t, (see, e.g., Reference 47). Thus, for example:

$$\langle \varepsilon_i^t \varepsilon_i^{tT} \rangle = \frac{1}{N_t} \sum_{t=1}^{N_t} \varepsilon_i^t \varepsilon_i^{tT} \quad (7)$$

for each of principal directions i (e.g., no summation over i can be implied). The principal eigenvector associated with the dyadic tensor can serve as the tissue orientation averaged over all t, where in the exemplary example $N_t$=8. FIG. 9A-FIG. 9I show exemplary images of compartments parameters derived from a diffusion tensor according to an exemplary embodiment of the present disclosure. The orientation and anisotropy can then be visualized by creating directionally-encoded FA ("DEC-FA") maps (see e.g., FIG. 9A-FIG. 9I), in which the median FA(t) can be multiplied by the principle eigenvector of $\langle \varepsilon_1^t \varepsilon_1^{tT} \rangle$.

The principle eigenvectors from $\langle \varepsilon_1^t \varepsilon_1^{tT} \rangle$, $\langle \varepsilon_2^t \varepsilon_2^{tT} \rangle$, and $\langle \varepsilon_3^t \varepsilon_3^{tT} \rangle$ for each compartment and the eigenvalues at t=105 ms were used to reconstruct the corresponding diffusion-weighted images. They were subsequently used as an input to perform fiber tractography using various suitable tool-boxes, for instance, with mrtrix 3.0 using probabilistic streamline tractography. The fibers from the cellular compartment can represent smooth muscle stroma, for which the structural anisotropy can be clear on histology. (See e.g., images shown in FIG. 1A). At each voxel, residual bootstrap was performed to obtain a specific realization of the dMRI data. The data was then resampled via trilinear interpolation at each streamline procedure. The diffusion tensor model was then applied and streamlines were drawn following the orientation of the principal eigenvector.

Exemplary Microstructural Modeling in Each Compartment
Exemplary Glandular Lumen: Short-Time S/V Limit In the lumen compartment, due to its large size, $D_{ij}^L(t)$ can be isotropic, and can fall into the short time regime, (see, e.g., Reference 48) such that, for example.

$$\overline{D}^L(t) \simeq D_0^L\left(1 - \frac{4}{3d\sqrt{\pi}}\frac{S}{V}\sqrt{D_0^L t}\right), \qquad (8)$$

$$\overline{D}^L(t) = \frac{1}{3}\sum_{i=1}^{3} D_{ii}^L(t)$$

where the mean diffusivity $\overline{D}^L(t)$ can be described solely by the surface-to-volume ratio ("S/V") of the lumen walls, and the intrinsic diffusivity $D_0^L$ in the glandular lumen can be close to free water value. The $\sqrt{t}$ scaling, Eq. (8), is shown in FIG. 7C. The lumen diameter $\alpha^L = 6V/S \approx 200$ μm in healthy glands can then be determined; this can also be applied for the prostate cancer cases, where glands generally become smaller. FIG. 10A-FIG. 10H show exemplary images, and corresponding exemplary graphs, of cellular and luminal parameters derived from D(t) according to an exemplary embodiment of the present disclosure.

The range of times over which the S/V limit in Eq. (8) can be applicable, and can be $t \ll l_{pore}^2/(2dD_0)$, where $l_{pore}$ can be the pore characteristic length scale; this estimate was validated in a phantom. (See, e.g., Reference 49). Assuming that glandular lumen can have $D_0 \approx 3$ μm²/ms (e.g., free water at body temperature), and diameter $l_{pore} \sim 100$ μm, the S/V limit can apply for $t \ll 500$ ms. This can indicate that the S/V limit can be applicable in the healthy glandular lumen over a broad t range. However, luminal diameters can shrink with tumor grade (see, e.g., References 36 and 50), which can shorten the range of t over which the S/V limit can be applicable in patients. The corrections to Eq. (2) can be used due to wall curvature or permeability.

Exemplary Long-Time Limit: D(t) as a Probe of Membrane Permeability and Structural Correlations In contrast to the luminal compartment, the cellular compartment can be densely packed and can contain cells with small approximately 10 μm diameters, which can shrink even further with increasing tumor grade. (See e.g., Reference 59). Assuming $D_0 \sim 1$ μm²/ms, locally in d=2-dimensions due to fibrous geometry (see e.g., Reference 34), the range over which the S/V limit can apply can be expected to be $t \leq 25$ ms. For clinically accessible t, diffusion in the cellular compartment can be acquired outside of the S/V limit. Exceeding this limit, the diffusion length can become comparable or greater than the characteristic length scale of the tissue (e.g., cell diameter), and D(t) can become dependent on numerous tissue parameters describing both cell geometry and membrane permeability.

To identify which features of tissue complexity can be beneficial for the measurement, it can be beneficial to observe time-dependent diffusion in the long time limit, approaching the bulk diffusion coefficient $D_\infty$. (See, e.g., Reference 52). Time-dependence in this limit can reveal an exemplary footprint of the underlying structure using the dynamical exponent $\vartheta$ in the instantaneous diffusion coefficient, which can be, for example:

$$D_{inst}(t) \equiv \frac{1}{2}\frac{\partial}{\partial t}\langle x^2(t)\rangle \simeq D_\infty + A \cdot t^{-\vartheta}, \; t \to \infty. \qquad (9)$$

Here, A can be the associated strength of the structural disorder, which can be effectively coarse-grained by the molecules traveling over an increasing diffusion length. The exponent $$\vartheta = (p+d)/2 \qquad (10)$$

can be related to the statistics of the global arrangement of tissue microstructure (e.g., stroma and epithelium cells) using the structural exponent p in d spatial dimensions. The exponent p can define the structural universality class (see, e.g., Reference 52) of random media. The larger the exponent p, the faster the structural fluctuations can decrease at large distances, and the more ordered the medium. This exponent can describe the low-k behavior of the power spectrum $\Gamma(k) \sim A k^p$ of the restrictions, corresponding to the decay of their density-density correlation function $$\Gamma(r) = \int \frac{d^d k}{(2\pi)^d} e^{ikr}\Gamma(k)$$

at large distances r. The Poissonian, and more generally, short-range disorder can correspond to p=0, strong disorder to p<0 (diverging fluctuations at large distances, for example, due to spatially extended restrictions) and hyperuniform disorder to p>0 (variance of fluctuations within a volume growing slower than the volume). (See, e.g., References 51 and 52). The gradual coarse-graining of the structure embodied in $\Gamma(r)$ over an increasing diffusion length $L(t) \sim r$ can result in the universal scaling, Eq. (9). Note that the dimensionality d of the diffusion process can be inferred from the shape of the diffusion tensor. In an isotropic case d=3, whereas, for instance, for an axially symmetric diffusion tensor (e.g., in tissue fibrous geometry), d=2 for the transverse and d=1 for the longitudinal diffusion eigenvalues $\lambda_\perp$ and $\lambda_\parallel$, correspondingly.

The universal asymptotic law of Eq. (9), with the relation of Eq. (10) between the structure and diffusive dynamics, can be used for exemplary model selection. However, dMRI can measure the cumulative $$D(t) = \frac{1}{t}\int_0^t D_{inst}(t')dt'.$$

Such temporal averaging can limit the range of directly-measurable exponents (e.g., without differentiating noisy data), since the corresponding long-time tail in D(t) can have the exponent $\tilde{\vartheta} = \min(\vartheta, 1)$. (See, e.g., Reference 52.

Structural order in any d, and hyperuniform disorder (p>0) in d≥2 dimensions can all have $\vartheta > 1$, which means that the tail in the cumulative D(t) can have exponent $\tilde{\vartheta} = 1$, masking the genuine $\vartheta$. Thus, for example:

$$D(t) \approx D_\infty + A \cdot t^{-1}, t \to \infty. \qquad (11)$$

Hyperuniform disorder can suppress structural fluctuations and can arise in optimal random packings. Hyperuniform disorder can be the closest to a perfectly periodic arrangement of the building blocks in a medium. Eq. (11) provides that any such arrangement (e.g. a periodic lattice of barriers, or the "crystal lattice" of identical cells) can yield the asymptotic $\sim 1/t$ behavior in D(t).

A similar-looking 1/t tail can arise when a tissue compartment can correspond to perfectly impermeable cells of size $\sim \sqrt{A}$ (e.g., fully restricting cell walls), placing a hard upper bound on $\langle x^2(t) \rangle$. This can be the simplest non-Gaussian compartment model. (See, e.g., References 57-58).

Short-range disorder in 2 dimensions (e.g., transverse to aligned fibers randomly packed in a bundle yields $\vartheta=1$ and the corresponding $\ln(t/\delta)/t$ tail in D(t), which, for the diffusion gradient pulse width $\delta > t_c$ exceeding the corresponding correlation time across the packing correlation length, can yield the following exemplary behavior:

$$D(t,\delta) \simeq D_\infty + \frac{A}{2\delta^2\left(t-\frac{\delta}{3}\right)}\left[t^2\ln\frac{t^2-\delta^2}{t^2} + \delta^2\ln\frac{t^2-\delta^2}{\delta^2} + 2t\delta\ln\frac{t+\delta}{t-\delta}\right], \quad (12)$$

$$t > \delta,$$

that asymptotically can become $A \ln(t/\delta)/t$ for $t \gg \delta$.

Extended-disorder (random membranes), for example, random lines in d=2 dimensions or randomly placed and oriented planes in d=3, can yield the slow power-law tail. (See, e.g., References 51-52). Thus, for example:

$$D(t) \simeq D_\infty + A \cdot t^{-\frac{1}{2}}, t \to \infty. \quad (13)$$

This disorder geometry can be approximately described for all t by the random permeable barrier model ("RPBM") based on the real-space renormalization group approach to the diffusion equation represented as a scattering problem. (See, e.g., References 51-55). The RPBM can be subsequently found to describe diffusion transverse to muscle fibers (d=2) (See, e.g., References 53-55), where diffusion along fibers can be practically unrestricted, while the transverse diffusion coefficient can strongly decrease with t.

There can be a subtle difference between Eqs. (12) and (13), as applied to the d=2 fiber geometry: Eq. (12) can apply if the fibers can be randomly packed in a bundle, hindering the extra-cellular water (e.g., a random packing of disks in the cross-section), yielding $\Gamma(k)$~const for $k \to 0$, for example, p=0, while Eq. (13) can apply if the cell walls appear to be locally flat (e.g., lines in the cross-section) and sufficiently permeable, so that the intra- and extra-cellular spaces can be considered on an equal footing. (See, e.g., Reference 60). The exponent ½ can arise due to the distinct spatial statistics of the restrictions, represented by the locally flat permeable membranes (e.g., fiber walls) that can extend for longer than the diffusion length, and yield the corresponding low-k divergence in $\Gamma(k)$~$k^{-1}$, as shown by the line 410 in FIG. 4A-FIG. 4D, which approaches $k^{-1}$, line 405, for perfectly straight random permeable barriers; the temporal scaling in Eq. (13) can emerge when these membranes can be traversed more than once during the diffusion time t.

There can be a measurable effect of a time-dependent D(t), which can differ between benign and various stages of peripheral zone cancer. (See, e.g., Reference 23). However, the relative compartment contributions to the overall D(t) were not separated. Partial volume effects can be overcome, so that the microstructure of intermixing tissue can be identified. By decomposing the dMRI signal into fast and slow $T_2$ compartments, exemplary model selection for D(t) within cellular and luminal tissues, can be performed independently, based on the above range of models of diffusion in disordered media.

Exemplary model selection can be performed by inferring the distinct functional form of the measured D(t), rather than relying on goodness-of-fit metrics which can be often misleading. By identifying the dynamical exponent in Eq. (10), or the short-time regime in Eq. (8), the tissue can reveal its type of structure (e.g., the S/V limit, or a structural universality class), instead of imposing a particular model of restricted diffusion from the outset. Identification of the disorder class can then justify searching for the most parsimonious model within that class. This can be based on the fact that structural complexity can be hierarchical; its most relevant degrees of freedom can be identified first (e.g., they define the signal's overall functional form), followed by fine-tuning the remaining microscopic details, SNR permitting.

Exemplary Stroma: D(t) as a Probe of Membrane Permeability and Fiber Diameter

The cellular compartment can be highly anisotropic (see, e.g., FIG. 6C and FIG. 10B), with the eigenvalue $\lambda_\parallel^C$ parallel to stromal fibers being approximately constant, whereas diffusion $\lambda_\perp^C(t)$ transverse to fibers can be strongly t-dependent, which can be indicative of restrictions. FIG. 4A-FIG. 4D show exemplary graphs and corresponding histopathologies for the structural correlation of stroma according to an exemplary embodiment of the present disclosure. As shown in FIG. 4A-FIG. 4D, these restrictions can be the permeable stroma fiber walls, which can be described by the exemplary random permeable barrier model ("RPBM") (see, e.g., References 51-55) with the following parameters: (i) intrinsic diffusion constant $D_0^C$ inside fibers; (ii) stromal fiber diameter $\alpha^C$; and (iii) its membrane permeability $\kappa$. The permeability can be used to determine the tissue's capacity for chemical transport related towards the tissue's susceptibility towards chemo/radiation therapy. The exemplary assumptions can be confirmed (i) by an agreement between $\alpha^C=4V/S$ derived from RPBM (see e.g., FIG. 10D) and found from prostate histology (see e.g., FIG. 4B-FIG. 4D); (ii) by the scaling $\Gamma(k)$~$k^{-1}$ of the power spectrum of fiber walls segmented from histology (see e.g., FIG. 4A-FIG. 4D), a RPBM assumption (see e.g., FIG. 6C; and (iii) by the corresponding ~$t^{-1/2}$ long-time behavior of $\lambda_\perp^C(t)$ (see e.g., FIG. 7C), a signature of RPBM. (See, e.g., Reference 51). This slow $t^{-1/2}$ decrease can contradict earlier assumptions of an impermeable compartment (e.g., that would yield ~$t^{-1}$ behavior). (See, e.g., References 39-41).

FIG. 5A shows an exemplary set of images of STEAM relaxometry for echo time and mixing time according to an exemplary embodiment of the present disclosure. FIG. 5B shows an exemplary graph fitting Eq. (2) after averaging over a peripheral zone ("PZ") according to an exemplary embodiment of the present disclosure. FIG. 5C shows a set of exemplary parametric maps of five fitted parameters according to an exemplary embodiment of the present disclosure. FIG. 5D shows a set of exemplary histograms of a distribution of relaxation parameters according to an exemplary embodiment of the present disclosure.

Epithelium: D(t) as a Probe of Round Impermeable Cells

For the epithelial compartment, if used distinctly from the stromal compartment (e.g., not joining the two into the cellular compartment), the exemplary system, method, and computer-accessible medium, can use the model of an impermeable compartment, for example, a spherical compartment. (See, e.g., References 56-58). The diffusion gradient pulse width $\delta$ can also vary, since the diffusion propagator within the impermeable (e.g., on the relevant NMR time scales) compartment can depend both on the diffusion time (e.g., the inter-pulse interval), and the gradient pulse width. Exemplary modeling of diffusion within a confined compartment of a given size and intrinsic diffusivity, can provide estimates for intrinsic diffusivity and epithelium cell size, which can be used as possible cancer biomarkers.

Exemplary IVIM: D(t) as a Probe of the Vascular Compartment

The exemplary system, method, and computer-accessible medium, according to an exemplary embodiment of the present disclosure, can be used to model the IVIM compartment with a pseudo diffusion tensor, which can be isotropic. Its time dependence, if detected, can signify its initial increase with the diffusion time, which can eventually level off to a constant. Utilizing the time dependence of the IVIM compartment can be used to determine the time scale for the vasculature (e.g., where the time increase switches to a plateau), which can be then translated into the vasculature gyration radius using the well-known relation between the diffusion length and diffusion time $l \approx \sqrt{2Dt}$.

ment weighting can imply that the selection of the most appropriate tissue model can be confounded by $T_E$. Partial volume between cellular and luminal compartments can be resolved before modeling D(t) can reflect tissue specific length scales. For example, when applying RPBM or S/V limit models to D(t), the calculated length scale, a=4/(S/V), increased with $T_E$. Using compartment weighting to decompose the diffusion representation into cellular and luminal tensors can reveal a particular contrast as well; the maps of $\overline{D}^C$ appear smooth, whereas the $\overline{D}^L$ has higher diffusivity localized around PZ, a region that is dense with glandular lumen.

TABLE 2

Pearson correlation coefficient, ρ, is used as a proxy for model selection at various echo time ($T_E$) and at separated cellular/luminal diffusion tensors. Averaged mean diffusivity ($\overline{D}$) or radial diffusivity ($\lambda_\perp$) across (A) volunteer peripheral zone (PZ) and (B) patient ROIs: PZ, transition zone (TZ), low grade PZ (3 + 3), intermediate grade PZ (3 + 4), and high grade PZ (≥4 + 3) were compared against short-time Eq. (8) S/V limit t → 0 and long-time limit ($t^{-1}$, ~log(t/δ)/t, $t^{-1/2}$) models, Eqs (9-13). The bolded p in each column displays the highest correlation with the ROI.

| (A) Pearson Correlation (ρ) on Volunteers | $T_E$ = 52 ms | $T_E$ = 115 ms | $T_E$ = 180 ms | Cellular | Luminal |
|---|---|---|---|---|---|
| $\overline{D}$ (t) vs. Equation (2) | 0.912 | 0.932 | 0.957 | 0.9476 | 0.916 |
| $\lambda_\perp$ (t) vs. Equation (5) | 0.925 | 0.703 | 0.617 | 0.9192 | 0.1796 |
| $\lambda_\perp$ (t) vs. Equation (6) | 0.955 | 0.765 | 0.693 | 0.9458 | 0.2315 |
| $\lambda_\perp$ (t) vs. Equation (7) | 0.972 | 0.817 | 0.757 | 0.9634 | 0.2794 |
| (B) Pearson Correlation (ρ) on patients from ref.(17) | PZ | TZ | 3 + 3 | 3 + 4 | ≥4 + 3 |
| $\overline{D}$ (t) vs. Equation (2) | 0.911 | 0.983 | 0.902 | 0.771 | 0.855 |
| $\lambda_\perp$ (t) vs. Equation (5) | 0.826 | 0.730 | 0.912 | 0.959 | 0.910 |
| $\lambda_\perp$ (t) vs. Equation (6) | 0.886 | 0.809 | 0.952 | 0.961 | 0.956 |
| $\lambda_\perp$ (t) vs. Equation (7) | 0.921 | 0.868 | 0.971 | 0.948 | 0.982 |

TABLE 1

The mean and standard deviation over a PZ ROI is shown for the relaxation parameters derived from $S|_{b=0}$.

| | Parameters | | | | |
|---|---|---|---|---|---|
| | $W(T_E)$ | f | $T_2^C$[ms] | $T_2^L$[ms] | $T_1$ [ms] | $R^2$ |
| Subject 1 (22 y/o) | [0.82, 0.66, 0.49] ± [0.11, 0.14, 0.18] | 0.91 ± 0.09 | 62.2 ± 14.46 | 269.95 ± 93.03 | 1014.7 ± 292.7 | 0.933 ± 0.064 |
| Subject 2 (28 y/o) | [0.91, 0.82, 0.69] ± [0.09, 0.14, 0.2] | 0.95 ± 0.06 | 62.75 ± 6.66 | 244.87 ± 88.95 | 857.97 ± 154.38 | 0.972 ± 0.037 |
| Subject 3 (32 y/o) | [0.91, 0.82, 0.66] ± [0.05, 0.12, 0.21] | 0.96 ± 0.03 | 55.65 ± 6.95 | 226.45 ± 85.94 | 824.02 ± 117.88 | 0.942 ± 0.038 |

Exemplary Specificity Towards Microstructure Arising from Dependence on Both t and $T_E$ The exemplary system, method and computer-accessible medium, according to an exemplary embodiment of the present disclosure, can utilize compartment weighting on modeling prostate diffusion. Although time-dependence can be apparent at individual $T_E$, the functional form of D(t) for different $T_E$ can reflect a different mixture of tissue microstructure. (See e.g., Table 2 below). This relative compart- The t-dependence, in combination with $T_E$, can aid in the identification of the relevant microstructural degrees of freedom, as the time dependence can provide the sensitivity to the cellular-level length scale and the spatial correlations of the restrictions. Having identified the relevant degrees of freedom for the compartmental D(t), various exemplary models can be used to obtain corresponding length scales and membrane permeability. Good agreement with existing histopathology for the luminal sizes (e.g., 300±120 μm) and myofiber diameters [19.81±1.18], as well as with previous measurements of $T_2$ volume fractions (e.g., $f_{fast}$>0.8 and $f_{slow}$<0.2), can indicate strong associations of compartment-specific properties with non-invasive magnetic resonance imaging parameters.

Due to the large differences between cellular and lumen $T_2$ values, the separation of only these tissue compartments can be examined. The "cellular" compartment which had a volume fractions f>0.9 was a combination of all non-luminal tissue subtypes. With more $T_E$ values included in an acquisition, more than two compartments can be distinguished (e.g., it can be possible to distinguish between lumen, stroma and epithelium, and possibly also IVIM compartments). The "cellular" compartment can be expected to split into more granular components, such as epithelium and stroma, with potentially different microstructural degrees of freedom, as described above.

Exemplary RPBM v. Fully Restricted Compartment (RSI, VERDICT)

Exemplary Model selection based solely on the goodness of fit can be unreliable. Given how "remarkably unremarkable" the dMRI signal can be, model selection can be challenging. The exemplary system, method and computer-accessible medium, according to an exemplary embodiment of the present disclosure, reveal subtle signatures of distinct classes of structural complexity, by choosing between them on an equal footing, rather than pre-conditioning towards a particular model. For Eqs. (11)-(13), the goodness of fit at low $T_E$ or in the cellular compartment were all consistently strong $\rho > 0.9$.

Previous modeling assumptions of diffusion were fully restricted by impermeable barriers (see, e.g., References 39-41), because this can be the easiest "nontrivial" model of diffusion, for which exact solutions for simple geometries (e.g., a spherical pore) have been derived. (See, e.g., References 57-58). However, a fully restricted compartment's asymptotic D(t) behavior, Eq. (11), may not be preferred by the goodness-of-fit (e.g., neither in volunteers nor in the clinical population), and, can indicate systematic temporal structure in the fit residuals. (See e.g., graphs shown in FIG. 7A-FIG. 7C). The cellular compartment's time dependence can be dominated by the extended disorder universality class, Eq. (13), corresponding to the RPBM.

Because fibromuscular stroma and epithelium can be lumped into a single cellular compartment, there can be a competition between different power law tails from different compartments. If, for instance, the epithelium compartment can be described by approximately impermeable cells, it may be practically impossible to distinguish its role in the overall "cellular" diffusivity time dependence as it can be asymptotically dominated by the smallest exponent $\vartheta = \frac{1}{2}$, $$c_{1/2} t^{-\frac{1}{2}} + c_1 t^{-1} \sim c_{1/2} t^{-\frac{1}{2}}, t \to \infty,$$

which can overshadow the effect of other compartments. To understand whether the fully restricted compartment can play a non-negligible role, the exemplary analysis can be repeated with N=3 or N=4 compartments, provided that the separation between epithelium and stroma (and possibly IVIM compartment) via their $T_2$ values can be practically achievable.

The dynamical exponent ½ can indicate the extended nature of the restrictions and their permeability as relevant degrees of freedom for diffusion in this tissue. Furthermore, it can be found that the cellular compartment can fall into the same disorder structural universality class as skeletal muscle. If restrictions in the cellular compartment can be largely dominated by fibromuscular stroma (e.g., smooth muscle), then the strong agreement with Eq. (13), which also best describes skeletal muscle. (See, e.g., References 51-55). Based on the exemplary permeability estimates, the effective membrane hindrance parameter $\zeta \sim 2.14 \pm 1.77$ may not be very large, which can indicate that the membranes can be quite leaky, which a posteriori an also justify neglecting the distinction between intra- and extra-cellular space in the RPBM. The average standard deviation in $D_\infty$ across all measurements was about 0.03 $\mu m^2/ms$, indicating that this can be a highly robust parameter. These consistent findings of a finite $D_\infty$ can be incompatible with the pictures of stretched-exponential diffusion signal, and anomalous diffusion in prostate.

Exemplary Effect of Intra-Compartmental Non-Gaussian Diffusion

Separating compartments via $T_2$ relaxation can be "orthogonal" to diffusion acquisition parameters b and t. This can indicate that the exemplary system, method and computer-accessible medium can be extended further to include higher order diffusion metrics, such as kurtosis, in each compartment, based on the distinct $T_2$ relaxation properties.

Given the appropriate range of $T_E$, estimating the NMR relaxation times via $S|_{b=0}$ ($T_M$, $T_E$) can be performed. The fitting was based on the large separation of compartmental $T_2$ values. However, $T_2$ can become shorter with increasing field strength. This can have an impact on diffusion measurements: the diffusion coefficient in the brain between 1.5 and 3T systems has been reported to have a variance of ~7%.

Exemplary Compartmental Anisotropy

Since the cellular compartment was found to be within the long-time limit, it can be possible to derive a meaningful interpretation of the diffusion tensor orientation. Fiber tracking can be performed on this compartment to characterize tissue anisotropy in 3-dimensions. Many areas do not display any track information, which can indicate that that (i) the fiber orientation was incoherent (e.g., FIG. 1A shows a histological cross section with axial and perpendicular stromal cross-sections), or (ii) the dataset was unable to resolve meaningful tracts. This can be expected as prostate imaging can be vulnerable to motion and distortion artifacts. While the rigid motion correction and the static distortion correction have been used, the image quality can still be imperfect. Thus, the only fiber tracks shown are the ones that were generated with high confidence. The luminal compartment can be far from the long-time limit, and thus no consistent orientation information can be apparent. This can provide additional confirmation that the luminal compartment for the exemplary data can be within the S/V limit. Note that lumen can be anisotropic (e.g., at sufficiently large length scales), but the acquisition may only become sensitive to their anisotropy at prohibitively long tin healthy subjects. The applicability of the S/V limit to the lumen compartment can be expected to change in patient populations as glandular lumen can shrink with increasing tumor grade. At higher tumor grade, characterization of orientation dependence in both the cellular and gland compartments may become feasible.

Exemplary Localization Regime for Model Validation and Parameter Estimation

Since the diffusion gradient G was not fixed with t, the diffusion weighting can be confounded by spatially variable spin dephasing (e.g., with the signal suppressed less next to, for example, lumen walls), which can be an orthogonal avenue of microstructure. (See, e.g., Reference 64). In the case of luminal diffusivities, D=3 $\mu m^2/ms$, the localization length in the exemplary experiment increased together with t, because of the decreasing gradient: $L_G = (D/\gamma G)^{1/3} = [5.83, 6.36, 6.93, 7.54, 8.22, 8.90, 9.64, 10.48]$ $\mu m$; the diffusion length $L_D = \sqrt{D\delta} = 4.47$ $\mu m$ was fixed. This can indicate that the exemplary experiment was performed in the "free-diffusion" regime ($L_G > L_D$), where the "localization regime" near the walls can have a relatively weak contribution towards echo decay. However, $L_G$ and $L_D$ can be fairly close to each other; therefore, there can be the choice of selecting for the free diffusion regime or the localization regime. The localization regime can be probed by varying G while setting $\delta \sim t$, or by varying $\delta$, with relatively high G, such that $L_D > L_G$. This can imply that strong diffusion gradients can be used to reach the localization regime, to magnify the contribution of glandular lumen walls, which can yield an estimate for their S/V ratio and the glandular lumen size within each voxel, as the signal can be proportional to a known power of S/V based on the lumen geometry.

The exemplary system, method and computer-accessible medium, according to an exemplary embodiment of the present disclosure, can be used to identify basic building blocks for a physical picture of water diffusion in prostate tissue microstructure, which can be used for in vivo diffusion MRI measurements in humans. Both diffusion and transverse NMR relaxation can be shown to include at least two biophysically distinct contributions, which can be attributed to glandular lumen (e.g., long $T_2$ and fast diffusion), and tissue, such as stroma, with short $T_2$ and heavily restricted anisotropic diffusion. These contributions can be further extended to other compartments, such as epithelium and stroma separately, as well as vascular IVIM.

The exemplary system, method and computer-accessible medium, according to an exemplary embodiment of the present disclosure, can facilitate a number of objective cellular-level tissue structure parameters as candidate markers for the non-invasive diagnosis and staging of prostate cancer with magnetic resonance imaging. The exemplary multi-dimensional MRI modeling procedure based on Eq. (1), as well as on compartment-specific microstructural models of time-dependent diffusion, can be generalized to other tissues and organs (e.g., liver, kidney, muscle, brain).

Figure 11A:
FIG. 11A and FIG. 11B are exemplary images of luminal ducts according to an exemplary embodiment of the present disclosure.
Figure 11B:
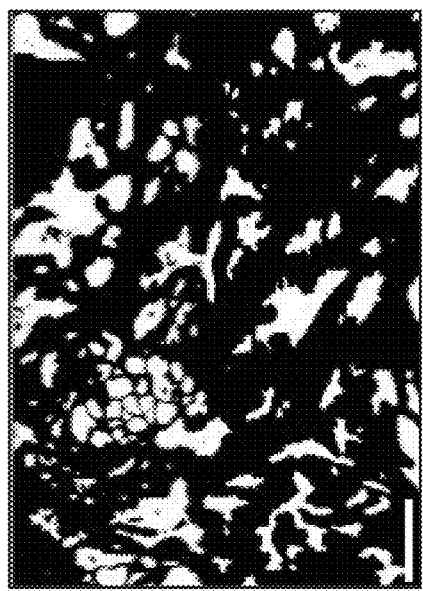
Figure 11C:
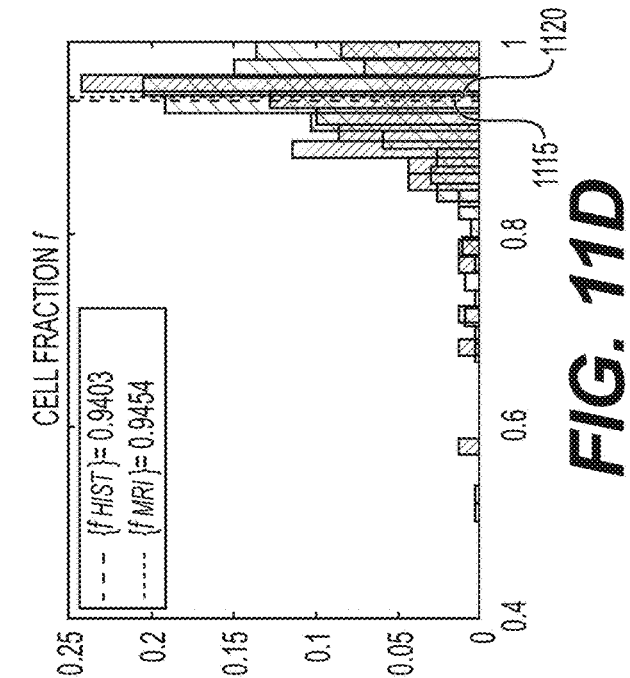
FIG. 11C and FIG. 11D are exemplary histograms corresponding to FIG. 11A and FIG. 11B, respectively, according to an exemplary embodiment of the present disclosure.
Figure 11D:
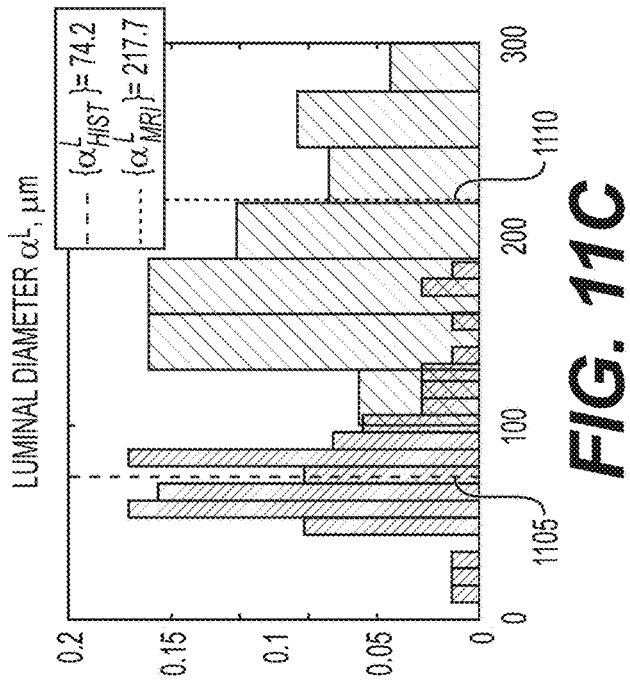

FIG. 11A and FIG. 11B are exemplary images of luminal ducts according to an exemplary embodiment of the present disclosure. In particular, FIG. 11A and FIG. 11B illustrate exemplary segmentations of luminal ducts from benign peripheral zone containing 1,000×1,400 pixels over a field of view of 2.4×3.4 mm², which were segmented using K-means clustering. 200 Å~200 non-overlapping pixel segments were sampled from these masks in order to determine the volume fraction (see e.g., Eq. (9)), with a surface-to-volume ratio, S/V=3/2 1/A, which was then used to approximate $\alpha_L^{hist}$=6V/S. The power-law exponent 3/2 was used to convert the 2-dimensional properties of histology into 3-dimensional units (e.g., in order to match the MRI results). This conversion approximately assumes a 3-dimensional cubic geometry within the luminal compartment. FIG. 11C and FIG. 11D show exemplary histograms corresponding to FIG. 11A and FIG. 11B, respectively, according to an exemplary embodiment of the present disclosure. Such exemplary histograms of FIG. 11C and FIG. 11D illustrate the median of each distribution comparing $\alpha_{HIST}^L$ (line 1105) to $\alpha_{MRI}^L$ (Line 1110) (see e.g., histogram shown in FIG. 11C) and $f_{HIST}$ (line 1115) to $f_{MRI}$ (line 1120) (see e.g., FIG. 11D), derived from MRI and histology. The histograms for MRI results are identical to distributions shown in FIG. 5D, for fMRI and FIG. 9A-FIG. 9I, for aLMRI.

$$f_{L,hist} = f_{L,A}^{3/2} \quad (14)$$

$\vec{q}$

The diffusion vector $\vec{q}$ can be varied with weighted and unweighted diffusion image (e.g., by varying the b-value and the diffusion direction). Mixing time $T_M$, can result in a higher information content protocol that can be used for finer changes in prostate microstructure. The compartmental and microstructural parameters (e.g., S($\vec{q}$, t, $T_E$, $T_M$) may not be determined from standard clinical acquisitions because such acquisitions do not contain enough information. To enhance the information content of an acquisition, varying at least one of the above sequence parameters (t, $T_E$, $T_M$) can be beneficial.

The exemplary system, method and computer-accessible medium, according to an exemplary embodiment of the present disclosure, can also utilize a series of weighted images, S($\vec{q}$, t, $T_E$, $T_M$), where at least one of t, $T_E$, $T_M$ can be varied, which can be used to empirically train a neural net or another general-purpose classifier (e.g., artificial intelligence or neural network, such as, a convolutional neural network), for the classification of prostate cancer grade. The output of such a classifier can be a composite image or a probability map of pathology location. The exemplary system, method and computer-accessible medium can be used to vary (t, $T_E$, $T_M$) in order to enhance the information content of the acquisition, even if the specific parametric maps are not explicitly derived.

Thus, the exemplary system, method and computer-accessible medium can include (i) a non-standard acquisition, where a clinical sequence with at least one of (t, $T_E$, $T_M$) can be varied, and not default values, with examples of parameter ranges provided above. Additionally, the compartmental fractions, T1/T2 relaxation times, and microstructural parameters can be generated. Using the exemplary system, method and computer-accessible medium, which can incorporate machine-learning classifiers such as neural nets, can improve diagnostic accuracy and value.

Figure 12A:
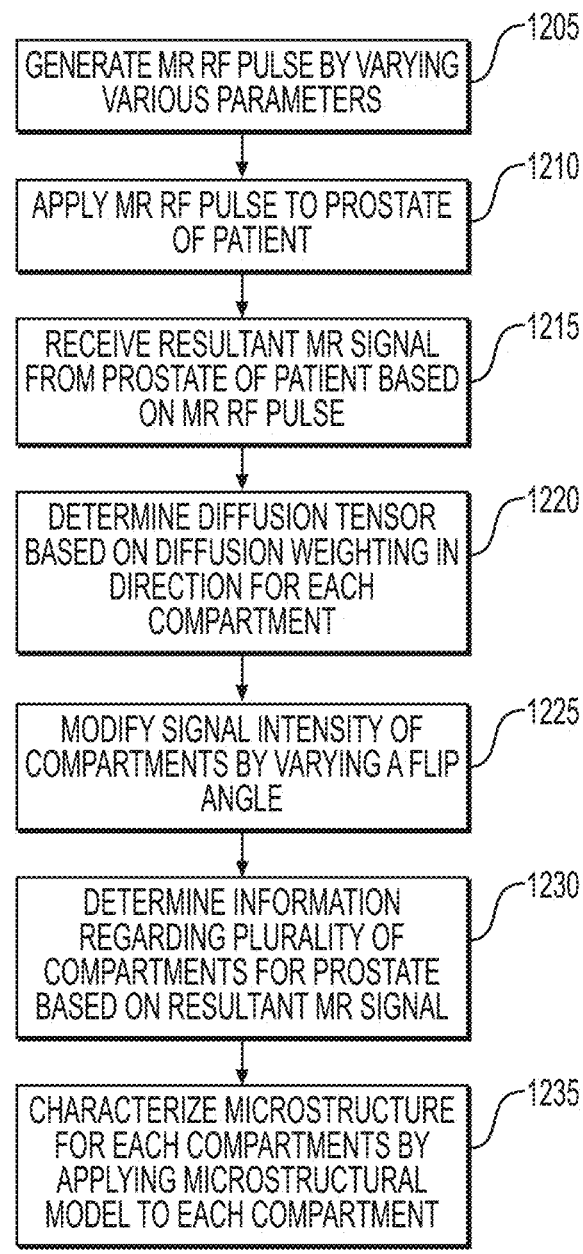
FIG. 12A is an exemplary method for characterizing a microstructure of a prostate of a patient according to an exemplary embodiment of the present disclosure.

FIG. 12A shows an exemplary method 1200 for characterizing a microstructure of a prostate of a patient according to an exemplary embodiment of the present disclosure. For example, as shown in FIG. 12A, at procedure 1205, a MR RF pulse can be generated by varying various exemplary parameters. At procedure 1210, the MR RF pulse can be applied to a prostate of a patient. At procedure 1215, a resultant MR signal can be received from the prostate of the patient that can be based on the MR RF pulse. At procedure 1220, a diffusion tensor can be determined based on a diffusion weighting in direction for each compartment. At procedure 1225, a signal intensity of the compartments can be modified by varying a flip angle. At procedure 1230, information regarding a plurality of compartments for a prostate can be determined, for example, from the resultant MR signal, as well as other parameters as described herein above (e.g., subvoxel intensity, diffusion tensors, etc.). At procedure 1235, a microstructure for each compartment can be determined/characterized by applying a microstructural model to each of the compartments by varying certain parameters.

Figure 12B:
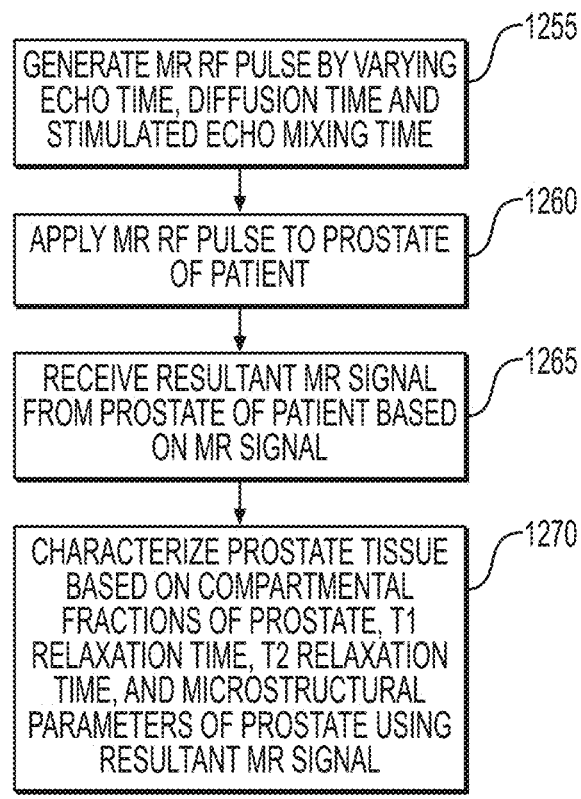
FIG. 12B is an exemplary method for characterizing prostate tissue of a prostate of a patient according to an exemplary embodiment of the present disclosure.

FIG. 12B shows an exemplary method 1250 for characterizing prostate tissue according to an exemplary embodiment of the present disclosure. For example, at procedure 1255, an MR RF pulse can be generated by varying at least one of: an echo time, a diffusion gradient or wave form, a diffusion time and a stimulated echo mixing time. At procedure 1260, the MR RF pulse can be applied to the prostate of a patient. At procedure 1265, a resultant MR signal can be received from the prostate of the patient based on the MR RF pulse. At procedure 1270, prostate tissue of the prostate can be characterized based on compartmental fractions of the prostate, a T1 relaxation time, a T2 relaxation time, and a microstructural parameters of prostate using the resultant MR signal.

Figure 13:
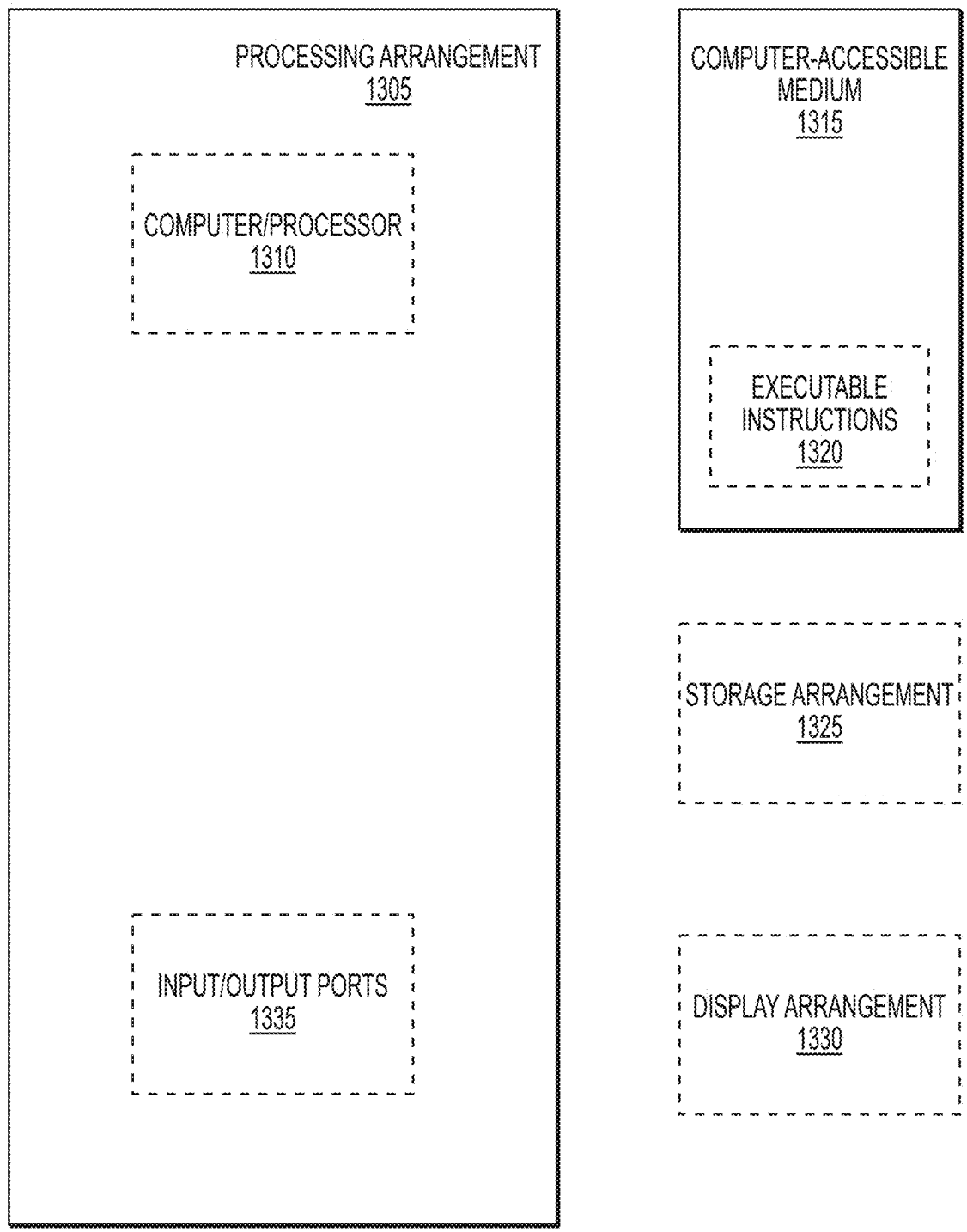
FIG. 13 is an illustration of an exemplary block diagram of an exemplary system in accordance with certain exemplary embodiments of the present disclosure.

FIG. 13 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 1305. Such processing/computing arrangement 1305 can be, for example entirely or a part of, or include, but not limited to, a computer/processor 1310 that can include, for example one or more microprocessors, and use instructions stored on a computer-accessible medium (e.g., RAM, ROM, hard drive, or other storage device).

As shown in FIG. 13, for example a computer-accessible medium 1315 (e.g., as described herein above, a storage device such as a hard disk, floppy disk, memory stick, CD-ROM, RAM, ROM, etc., or a collection thereof) can be provided (e.g., in communication with the processing arrangement 1305). The computer-accessible medium 1315 can contain executable instructions 1320 thereon. In addition, or alternatively, a storage arrangement 1325 can be provided separately from the computer-accessible medium 1315, which can provide the instructions to the processing arrangement 1305 so as to configure the processing arrangement to execute certain exemplary procedures, processes, and methods, as described herein above, for example.

Further, the exemplary processing arrangement 1305 can be provided with or include an input/output ports 1335, which can include, for example a wired network, a wireless network, the internet, an intranet, a data collection probe, a sensor, etc. As shown in FIG. 13, the exemplary processing arrangement 1305 can be in communication with an exemplary display arrangement 1330, which, according to certain exemplary embodiments of the present disclosure, can be a touch-screen configured for inputting information to the processing arrangement in addition to outputting information from the processing arrangement, for example. Further, the exemplary display arrangement 1330 and/or a storage arrangement 1325 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference, in their entireties:

1. Cancer Facts & Figures. American Cancer Society 2018; https://www.cancer.org/cancer/prostate-cancer/about/key-statistics.html.
2. Albertsen P C. Treatment of localized prostate cancer: when is active surveillance appropriate? Nat Rev Clin Oncol 2010; 7:394-400.
3. Schroder F H, Hugosson J, Roobol M J, et al. Screening and prostate-cancer mortality in a randomized European study. N Engl J Med 2009; 360:1320-8.
4. Pardo Y, Guedea F, Aguilo F, et al. Quality-of-life impact of primary treatments for localized prostate cancer in patients without hormonal treatment. J Clin Oncol 2010; 28:4687-96.
5. Mufarrij P, Sankin A, Godoy G, Lepor H. Pathologic outcomes of candidates for active surveillance undergoing radical prostatectomy. Urology 2010; 76:689-92.
6. Albertsen P. Further Support for Active Surveillance in the Management of Low-Volume, Low-Grade Prostate Cancer. Eur Urol 2010.
7. Kitajima K, Kaji Y, Kuroda K, Sugimura K. High b-value diffusion-weighted imaging in normal and malignant peripheral zone tissue of the prostate: effect of signal-to-noise ratio. Magnetic resonance in medical sciences: MRMS: an official journal of Japan Society of Magnetic Resonance in Medicine 2008; 7:93-9.
8. Somford D M, Hambrock T, Kaa C A H-vd, et al. Initial Experience With Identifying High-grade Prostate Cancer Using Diffusion-weighted Mr Imaging (dwi) in Patients With a Gleason Score≤3+3=6 Upon Schematic Trus-guided Biopsy: A Radical Prostatectomy Correlated Series. Investigative Radiology 2012; 47:153-8.
9. Hambrock T, Hoeks C, Hulsbergen-van de Kaa C, et al. Prospective Assessment of Prostate Cancer Aggressiveness Using 3-T Diffusion-Weighted Magnetic Resonance Imaging—Guided Biopsies Versus a Systematic 10-Core Transrectal Ultrasound Prostate Biopsy Cohort. European Urology 2012; 61:177-84.
10. Haider M A, van der Kwast T H, Tanguay J, et al. Combined T2-Weighted and Diffusion-Weighted MRI for Localization of Prostate Cancer. American Journal of Roentgenology 2007; 189:323-8.
11. Hassanzadeh E, Glazer D I, Dunne R M, Fennessy F M, Harisinghani M G, Tempany C M. Prostate imaging reporting and data system version 2 (PI-RADS v2): a pictorial review. Abdom Radiol (NY) 2017; 42:278-89.
12. Hoeks C M, Barentsz J O, Hambrock T, et al. Prostate cancer: multiparametric M R imaging for detection, localization, and staging. Radiology 2011; 261:46-66.
13. Chatterjee A, Watson G, Myint E, Sved P, McEntee M, Bourne R. Changes in Epithelium, Stroma, and Lumen Space Correlate More Strongly with Gleason Pattern and Are Stronger Predictors of Prostate ADC Changes than Cellularity Metrics. Radiology 2015; 277:751-62.
14. Gibbs P, Liney G P, Pickles M D, Zelhof B, Rodrigues G, Turnbull L W. Correlation of ADC and T2 measurements with cell density in prostate cancer at 3.0 Tesla. Invest Radiol 2009; 44:572-6.
15. Surov A, Meyer H J, Wienke A. Correlation between apparent diffusion coefficient (ADC) and cellularity is different in several tumors: a meta-analysis. Oncotarget 2017.
16. Zelhof B, Pickles M, Liney G, et al. Correlation of diffusion-weighted magnetic resonance data with cellularity in prostate cancer. BJU Int 2009; 103:883-8.
17. van As N J, de Souza N M, Riches S F, et al. A study of diffusion-weighted magnetic resonance imaging in men with untreated localised prostate cancer on active surveillance. Eur Urol 2009; 56:981-7.
18. Park S Y, Kim C K, Park B K, Lee H M, Lee K S. Prediction of biochemical recurrence following radical prostatectomy in men with prostate cancer by diffusion-weighted magnetic resonance imaging: initial results. Eur Radiol 2011; 21:1111-8.

19. Novikov D S, Kiselev V G, Jespersen S N. On modeling. Magnetic Resonance in Medicine 2018; 79:3172-93.
20. Novikov D S, Jespersen S N, Kiselev V G, Fieremans E. Quantifying brain microstructure with diffusion MRI: Theory and parameter estimation: Preprint arXiv: 1612.02059; 2016.
21. Kiselev V G. Fundamentals of diffusion MRI physics. NMR in Biomedicine 2017; 30:e3602-e.
22. Lemberskiy G, Fieremans E, Veraart J, Deng F-M, Rosenkrantz A B, Novikov D S. Characterization of prostate microstructure using water diffusion and NMR relaxation. Frontiers in Physics (under revision); Proc ISMRM 2018 (oral presentation) 2018.
23. Lemberskiy G, Rosenkrantz A B, Veraart J, Taneja S S, Novikov D S, Fieremans E. Time-Dependent Diffusion in Prostate Cancer. Invest Radiol 2017.
24. Merisaari H, Movahedi P, Perez I M, et al. Fitting methods for intravoxel incoherent motion imaging of prostate cancer on region of interest level: Repeatability and gleason score prediction. Magn Reson Med 2017; 77:1249-64.
25. Feng Z, Min X, Margolis D J, et al. Evaluation of different mathematical models and different b-value ranges of diffusion-weighted imaging in peripheral zone prostate cancer detection using b-value up to 4500 s/mm2. PLoS One 2017; 12:e0172127.
26. Quentin M, Blondin D, Klasen J, et al. Comparison of different mathematical models of diffusion-weighted prostate M R imaging. Magn Reson Imaging 2012; 30:1468-74.
27. Bourne R M, Panagiotaki E, Bongers A, Sved P, Watson G, Alexander D C. Information theoretic ranking of four models of diffusion attenuation in fresh and fixed prostate tissue ex vivo. Magn Reson Med 2014; 72:1418-26.
28. Jambor I, Merisaari H, Taimen P, et al. Evaluation of different mathematical models for diffusion-weighted imaging of normal prostate and prostate cancer using high b-values: a repeatability study. Magn Reson Med 2015; 73:1988-98.
29. Kjaer L, Thomsen C, Iversen P, Henriksen O. In vivo estimation of relaxation processes in benign hyperplasia and carcinoma of the prostate gland by magnetic resonance imaging. Magn Reson Imaging 1987; 5:23-30.
30. Storas T H, Gjesdal K I, Gadmar O B, Geitung J T, Klow N E. Prostate magnetic resonance imaging: multiexponential T2 decay in prostate tissue. J Magn Reson Imaging 2008; 28:1166-72.
31. Gilani N, Rosenkrantz A B, Malcolm P, Johnson G. Minimization of errors in biexponential T2 measurements of the prostate. J Magn Reson Imaging 2015; 42:1072-7.
32. Sabouri S, Chang S D, Savdie R, et al. Luminal Water Imaging: A New MR Imaging T2 Mapping Technique for Prostate Cancer Diagnosis. Radiology 2017; 284:451-9.
33. Sabouri S, Fazli L, Chang S D, et al. MR measurement of luminal water in prostate gland: Quantitative correlation between MRI and histology. J Magn Reson Imaging 2017.
34. Bourne R M, Kurniawan N, Cowin G, et al. Microscopic diffusivity compartmentation in formalin-fixed prostate tissue. Magn Reson Med 2012; 68:614-20.
35. Gorelick L, Veksler O, Gaed M, et al. Prostate histopathology: learning tissue component histograms for cancer detection and classification. IEEE Trans Med Imaging 2013; 32:1804-18.
36. Gilani N, Malcolm P, Johnson G. A monte carlo study of restricted diffusion: Implications for diffusion MRI of prostate cancer. Magn Reson Med 2017; 77:1671-7.
37. Novikov D S, Kiselev V G. Effective medium theory of a diffusion-weighted signal. NMR Biomed 2010; 23:682-97.
38. Chatterjee A, Bourne R M, Wang S, et al. Diagnosis of Prostate Cancer with Noninvasive Estimation of Prostate Tissue Composition by Using Hybrid Multidimensional MR Imaging: A Feasibility Study. Radiology 2018; 287: 864-73.
39. Brunsing R L, Schenker-Ahmed N M, White N S, et al. Restriction spectrum imaging: An evolving imaging biomarker in prostate MRI. J Magn Reson Imaging 2017; 45:323-36.
40. Rakow-penner R A, White N S, Parsons J K, et al. Novel technique for characterizing prostate cancer utilizing MRI restriction spectrum imaging: proof of principle and initial clinical experience with extraprostatic extension. 2015; 18:81-5.
41. Panagiotaki E, Chan R W, Dikaios N, et al. Microstructural characterization of normal and malignant human prostate tissue with vascular, extracellular, and restricted diffusion for cytometry in tumours magnetic resonance imaging. Investigative radiology 2015; 50:218-27.
42. Barrett T, Vargas H A, Akin O, Goldman D A, Hricak H. Value of the hemorrhage exclusion sign on T1-weighted prostate M R images for the detection of prostate cancer. Radiology 2012; 263:751-7.
43. Veraart J, Sijbers J, Sunaert S, Leemans A, Jeurissen B. Weighted linear least squares estimation of diffusion MRI parameters: strengths, limitations, and pitfalls. Neuroimage 2013; 81:335-46.
44. Basser P J, Mattiello J, LeBihan D. Estimation of the effective self-diffusion tensor from the NMR spin echo. Journal of Magnetic Resonance Series B 1994; 103:247-54.
45. Jones D K. Diffusion MRI: theory, methods, and application. Oxford; New York: Oxford University Press; 2010.
46. Bourne R, Liang S, Panagiotaki E, Bongers A, Sved P, Watson G. Measurement and modeling of diffusion time dependence of apparent diffusion coefficient and fractional anisotropy in prostate tissue ex vivo. NMR Biomed 2017.
47. Jones D K. Determining and visualizing uncertainty in estimates of fiber orientation from diffusion tensor MRI. Magn Reson Med 2003; 49:7-12.
48. Mitra P P, Sen P N, Schwartz L M. Short-time behavior of the diffusion coefficient as a geometrical probe of porous media. Physical Review B 1993; 47:8565-74.
49. Lemberskiy G, Baete S H, Cloos M A, Novikov D S, Fieremans E. Validation of surface-to-volume ratio measurements derived from oscillating gradient spin echo on a clinical scanner using anisotropic fiber phantoms. NMR Biomed 2017; 30.
50. Sabouri S, Fazli L, Chang S D, et al. Correction for geometric distortion in echo planar images from B O field variations. Magn Reson Med 2017; 76:883-8.
51. Novikov D S, Fieremans E, Jensen R I, Helpern J A. Random walks with barriers. Nature Physics 2011; 7:508-14.
52. Novikov D S, Jensen R I, Helpern J A, Fieremans E. Revealing mesoscopic structural universality with diffusion. Proc Natl Acad Sci USA 2014; 111:5088-93.
53. Sigmund E E, Novikov D S, *Sui* D, et al. Time-dependent diffusion in skeletal muscle with the random permeable barrier model (RPBM): application to normal controls and chronic exertional compartment syndrome patients. NMR Biomed 2014; 27:519-28.

54. Fieremans E, Lemberskiy G, Veraart J, Sigmund E E, Gyftopoulos S, Novikov D S. In vivo measurement of membrane permeability and myofiber size in human muscle using time-dependent diffusion tensor imaging and the random permeable barrier model. NMR Biomed 2017; 30.
55. Winters K V, Reynaud O, Novikov D S, Fieremans E, Kim S G. Quantifying myofiber integrity using diffusion MRI and random permeable barrier modeling in skeletal muscle growth and Duchenne muscular dystrophy model in mice. Magn Reson Med 2018.
56. Stepisnik J, T. Callaghan P. Long time tail of molecular velocity correlation in a confined fluid: Observation by modulated gradient spin-echo NMR2000.
57. Murday J S, Cotts R M. Self-Diffusion Coefficient of Liquid Lithium. The Journal of Chemical Physics 1968; 48:4938-45.
58. Neuman C H. Spin echo of spins diffusing in a bounded medium. The Journal of Chemical Physics 1974; 60:4508-11.
59. Delahunt B, Grignon D J, Samaratunga H, et al. Prostate Cancer Grading: A Decade After the 2005 Modified Gleason Grading System. Arch Pathol Lab Med 2017; 141:182-3.
60. Burcaw L M, Fieremans E, Novikov D S. Mesoscopic structure of neuronal tracts from time-dependent diffusion. Neuroimage 2015; 114:18-37.
61. Reynaud O, Winters K V, Hoang D M, Wadghiri Y Z, Novikov D S, Kim S G. Pulsed and oscillating gradient MRI for assessment of cell size and extracellular space (POMACE) in mouse gliomas. NMR Biomed 2016; 29:1350-63.
62. Reynaud O. Time-Dependent Diffusion MRI in Cancer: Tissue Modeling and Applications. Frontiers in Physics 2017; 5.
63. Merisaari H, Movahedi P, Perez I M, Toivonen J, Pesola M, Taimen P, Bostrom P J, Pahikkala T, Kiviniemi A, Aronen H J, Jambor I. Fitting methods for intravoxel incoherent motion imaging of prostate cancer on region of interest level: Repeatability and gleason score prediction. Magn Reson Med 2017; 77(3):1249-1264.
64. Stoller S D, Happer W, Dyson F J. Transverse spin relaxation in ihomogeneous magnetic fields. Phys Rev A 1991; 44:7459.

What is claimed is:

1. A non-transitory computer-accessible medium having stored thereon computer-executable instructions for characterizing a microstructure of a prostate of a patient, wherein, when a computer arrangement executes the instructions, the computer arrangement is configured to perform procedures comprising:

generating at least one magnetic resonance (MR) radiofrequency (RF) pulse by varying at least one of (i) a diffusion time, (ii) a diffusion gradient strength, (iii) a diffusion gradient direction, (iv) a diffusion gradient pulse width, (v) a diffusion gradient pulse shape, (vi) an echo time, (vii) a mixing time, or (viii) a flip angle;

applying the at least one MR RF pulse to the prostate of the patient;

receiving a resultant MR signal from the prostate of the patient that is based on the at least one MR RF pulse;

determining information regarding a plurality of compartments for the prostate from the resultant MR signal, wherein the compartments are specific models of biological or anatomical structures which include at least one tissue of the prostate; and characterizing the microstructure for each of the compartments by applying at least one microstructural model to each of the compartments, wherein the at least one microstructure model includes a plurality of microstructure models, and wherein each of the microstructure models is associated with one of the compartments, and wherein the computer arrangement is configured to determine the information regarding the compartments by estimating a fraction, relaxation times, and a diffusion tensor for each of the compartments based on the varied at least one of (i) the diffusion time, (ii) the diffusion gradient direction, (iii) the diffusion gradient pulse width, or (iv) the diffusion gradient pulse shape.

2. A method for characterizing a microstructure of a prostate of a patient, comprising:

generating at least one magnetic resonance (MR) radiofrequency (RF) pulse by varying at least one of (i) a diffusion time, (ii) a diffusion gradient strength, (iii) a diffusion gradient direction, (iv) a diffusion gradient pulse width, (v) a diffusion gradient pulse shape, (vi) an echo time, (vii) a mixing time, or (viii) a flip angle;

applying the at least one MR RF pulse to the prostate of the patient;

receiving a resultant MR signal from the prostate of the patient that is based on the at least one MR RF pulse;

determining information regarding a plurality of compartments for the prostate from the resultant MR signal, wherein the compartments are biological or anatomical compartments;

using a computer hardware arrangement, characterizing the microstructure for each of the compartments by applying at least one microstructural model to each of the compartments, wherein the at least one microstructure model includes a plurality of microstructure models, and wherein each of the microstructure models is associated with one of the compartments; and using the computer arrangement, determining the information regarding the compartments by estimating a fraction, relaxation times, and a diffusion tensor for each of the compartments based on the varied at least one of (i) the diffusion time, (ii) the diffusion gradient direction, (iii) the diffusion gradient pulse width, or (iv) the diffusion gradient pulse shape.

3. A system for characterizing a microstructure of a prostate of a patient, comprising:

a computer hardware arrangement configured to:

generate at least one magnetic resonance (MR) radiofrequency (RF) pulse by varying at least one of (i) a diffusion time, (ii) a diffusion gradient strength, (iii) a diffusion gradient direction, (iv) a diffusion gradient pulse width, (v) a diffusion gradient pulse shape, (vi) an echo time, (vii) a mixing time, or (viii) a flip angle;

apply the at least one MR RF pulse to the prostate of the patient;

receive a resultant MR signal from the prostate of the patient that is based on the at least one MR RF pulse;

determine information regarding a plurality of compartments for the prostate from the resultant MR signal, wherein the compartments are specific models of biological or anatomical structures which include at least one tissue of the prostate;

characterize the microstructure for each of the compartments by applying at least one microstructural model to each of the compartments, wherein the at least one microstructure model includes a plurality of microstructure models, and wherein each of the microstructure models is associated with one of the compartments; and determine the information regarding the compartments by estimating a fraction, relaxation times, and a diffusion tensor for each of the compartments based on the varied at least one of (i) the diffusion time, (ii) the diffusion gradient direction, (iii) the diffusion gradient pulse width, or (iv) the diffusion gradient pulse shape.

4. A non-transitory computer-accessible medium having stored thereon computer-executable instructions for characterizing a microstructure of a prostate of a patient, wherein, when a computer arrangement executes the instructions, the computer arrangement is configured to perform procedures comprising:

generating at least one magnetic resonance (MR) radiofrequency (RF) pulse by varying at least one of (i) a diffusion time, (ii) a diffusion gradient strength, (iii) a diffusion gradient direction, (iv) a diffusion gradient pulse width, (v) a diffusion gradient pulse shape, (vi) an echo time, (vii) a mixing time, or (viii) a flip angle;

applying the at least one MR RF pulse to the prostate of the patient;

receiving a resultant MR signal from the prostate of the patient that is based on the at least one MR RF pulse;

determining information regarding a plurality of compartments for the prostate from the resultant MR signal, wherein the compartments are specific models of biological or anatomical structures which include at least one tissue of the prostate; and characterizing the microstructure for each of the compartments by applying at least one microstructural model to each of the compartments, wherein the computer arrangement is configured to determine the information regarding the compartments by estimating at least one of (i) a glandular lumen surface-to-volume ratio, (ii) a glandular lumen size, (iii) a glandular lumen free diffusivity, (iv) a stromal surface-to-volume ratio, (v) a stromal fiber diameter, (vi) a stromal membrane permeability, (vii) a stromal intrinsic diffusivity, (viii) an epithelium cell size, or (ix) an epithelium free diffusivity, and wherein the computer arrangement is configured to determine the information regarding the compartments by estimating a fraction, relaxation times, and a diffusion tensor for each of the compartments based on the varied at least one of (i) the diffusion time, (ii) the diffusion gradient direction, (iii) the diffusion gradient pulse width, or (iv) the diffusion gradient pulse shape.

5. A method for characterizing a microstructure of a prostate of a patient, comprising:

generating at least one magnetic resonance (MR) radiofrequency (RF) pulse by varying at least one of (i) a diffusion time, (ii) a diffusion gradient strength, (iii) a diffusion gradient direction, (iv) a diffusion gradient pulse width, (v) a diffusion gradient pulse shape, (vi) an echo time, (vii) a mixing time, or (viii) a flip angle;

applying the at least one MR RF pulse to the prostate of the patient;

receiving a resultant MR signal from the prostate of the patient that is based on the at least one MR RF pulse;

determining information regarding a plurality of compartments for the prostate from the resultant MR signal, wherein the compartments are specific models of biological or anatomical structures which include at least one tissue of the prostate;

using a computer hardware arrangement, characterizing the microstructure for each of the compartments by applying at least one microstructural model to each of the compartments, wherein the information regarding the compartments is determined by estimating at least one of (i) a glandular lumen surface-to-volume ratio, (ii) a glandular lumen size, (iii) a glandular lumen free diffusivity, (iv) a stromal surface-to-volume ratio, (v) a stromal fiber diameter, (vi) a stromal membrane permeability, (vii) a stromal intrinsic diffusivity, (viii) an epithelium cell size, or (ix) an epithelium free diffusivity; and using the computer arrangement, determining the information regarding the compartments by estimating a fraction, relaxation times, and a diffusion tensor for each of the compartments based on the varied at least one of (i) the diffusion time, (ii) the diffusion gradient direction, (iii) the diffusion gradient pulse width, or (iv) the diffusion gradient pulse shape.

6. A system for characterizing a microstructure of a prostate of a patient, comprising:

a computer hardware arrangement configured to:

generate at least one magnetic resonance (MR) radiofrequency (RF) pulse by varying at least one of (i) a diffusion time, (ii) a diffusion gradient strength, (iii) a diffusion gradient direction, (iv) a diffusion gradient pulse width, (v) a diffusion gradient pulse shape, (vi) an echo time, (vii) a mixing time, or (viii) a flip angle;

apply the at least one MR RF pulse to the prostate of the patient;

receive a resultant MR signal from the prostate of the patient that is based on the at least one MR RF pulse;

determine information regarding a plurality of compartments for the prostate from the resultant MR signal, wherein the compartments are specific models of biological or anatomical structures which include at least one tissue of the prostate; and characterize the microstructure for each of the compartments by applying at least one microstructural model to each of the compartments, wherein the computer hardware arrangement is configured to determine the information regarding the compartments by estimating at least one of (i) a glandular lumen surface-to-volume ratio, (ii) a glandular lumen size, (iii) a glandular lumen free diffusivity, (iv) a stromal surface-to-volume ratio, (v) a stromal fiber diameter, (vi) a stromal membrane permeability, (vii) a stromal intrinsic diffusivity, (viii) an epithelium cell size, or (ix) an epithelium free diffusivity, and wherein the computer hardware arrangement is configured to determine the information regarding the compartments by estimating a fraction, relaxation times, and a diffusion tensor for each of the compartments based on the varied at least one of (i) the diffusion time, (ii) the diffusion gradient direction, (iii) the diffusion gradient pulse width, or (iv) the diffusion gradient pulse shape.

7. The computer-accessible medium of claim 1, wherein the computer arrangement is further configured to determine the diffusion tensor based on a diffusion weighting in a direction for each of the compartments.

8. The computer-accessible medium of claim 1, wherein the compartments include (i) a glandular lumen compartment, (ii) a stroma compartment, (iii) an epithelium compartment, or (iv) a vascular compartment.

9. The computer-accessible medium of claim 1, wherein the computer arrangement is configured to determine the information regarding the compartments by estimating at least one of (i) a glandular lumen surface-to-volume ratio, (ii) a glandular lumen size, or (iii) a glandular lumen free diffusivity.

10. The computer-accessible medium of claim 1, wherein the computer arrangement is further configured to determine the information regarding the compartments by estimating at least one of (i) a stromal surface-to-volume ratio, (ii) a stromal fiber diameter, (iii) a stromal membrane permeability, or (iv) a stromal intrinsic diffusivity.

11. The computer-accessible medium of claim 1, wherein the computer arrangement is further configured to determine the information regarding the compartments by estimating at least one of (i) an epithelium cell size or (ii) an epithelium free diffusivity.

12. The computer-accessible medium of claim 1, wherein the computer arrangement is configured to determine the information regarding the compartments by estimating at least one of (i) IntraVoxel Incoherent Motion ("IVIM") compartment fraction, (ii) an IVIM diffusion tensor, (iii) an IVIM diffusion coefficient, (iv) a characteristic time scale of time-dependent IVIM diffusion tensor.

13. The computer-accessible medium of claim 1, wherein each of the compartments includes its own set of markers.

14. The computer-accessible medium of claim 1, wherein the computer arrangement is further configured to determine the information regarding the compartments based on a compartment fraction of each of the compartments.

15. The computer-accessible medium of claim 14, wherein a sum of the compartment fraction for each of the compartments adds up to 1.

16. The computer-accessible medium of claim 1, wherein the computer arrangement is further configured to determine the information regarding the compartments based on a signal contribution of each of the compartments.

17. The computer-accessible medium of claim 16, wherein a signal intensity of the compartments is proportional to a proton density of the compartments.

18. The computer-accessible medium of claim 17, wherein the computer arrangement is further configured to modify the signal intensity by varying a flip angle.

19. The computer-accessible medium of claim 1, wherein the MRI signal is based on an estimated compartment weight for each of the compartments.

20. The computer-accessible medium of claim 1, wherein the computer arrangement is further configured to determine the compartments based on intra-compartment diffusion non-Gaussianity.

21. The computer-accessible medium of claim 1, wherein the computer arrangement is further configured to determine the compartments based on a plurality of diffusion gradient waveforms.

22. The computer-accessible medium of claim 1, wherein the compartments have distinct NMR relaxation properties.

23. The computer-accessible medium of claim 1, wherein the specific models use specific assumptions for the at least one tissue structure of the prostate.

\* \* \* \* \*